(12) United States Patent
Griffiths et al.

(10) Patent No.: US 7,776,065 B2
(45) Date of Patent: Aug. 17, 2010

(54) END EFFECTOR MECHANISM FOR A SURGICAL INSTRUMENT

(75) Inventors: Jerry R. Griffiths, Pembroke, MA (US); Francis J. DiFrancesco, Foxboro, MA (US)

(73) Assignee: Symmetry Medical New Bedford Inc, New Bedford, MA (US)

( * ) Notice: Subject to any disclaimer, the term of this patent is extended or adjusted under 35 U.S.C. 154(b) by 329 days.

(21) Appl. No.: 11/859,856

(22) Filed: Sep. 24, 2007

(65) Prior Publication Data
US 2008/0234725 A1 Sep. 25, 2008

Related U.S. Application Data

(60) Provisional application No. 60/895,760, filed on Mar. 20, 2007.

(51) Int. Cl.
*A61B 17/00* (2006.01)
(52) U.S. Cl. ...................................... 606/207
(58) Field of Classification Search .......... 606/205–211
See application file for complete search history.

(56) References Cited

U.S. PATENT DOCUMENTS

| | | | |
|---|---|---|---|
| 5,258,006 A | 11/1993 | Rydell et al. | |
| 5,261,918 A | 11/1993 | Phillips et al. | |
| 5,308,358 A | 5/1994 | Bond et al. | |
| 5,368,606 A | 11/1994 | Marlow et al. | |
| 5,649,957 A | 7/1997 | Levin | |
| 5,713,919 A | 2/1998 | Lahr | |
| 5,728,121 A | 3/1998 | Bimbo et al. | |
| 5,735,857 A * | 4/1998 | Lane | 606/99 |
| 6,238,414 B1 * | 5/2001 | Griffiths | 606/205 |
| 6,443,944 B1 * | 9/2002 | Doshi et al. | 606/1 |
| 6,582,465 B2 | 6/2003 | Marucci et al. | |
| 2002/0072766 A1 * | 6/2002 | Hunt et al. | 606/205 |
| 2008/0147113 A1 * | 6/2008 | Nobis et al. | 606/205 |

\* cited by examiner

*Primary Examiner*—Todd E Manahan
*Assistant Examiner*—Christopher Schubert
(74) *Attorney, Agent, or Firm*—AKC Patents LLC; Aliki K. Collins

(57) ABSTRACT

Improved end effector mechanisms for a surgical instrument used in minimally invasive surgical instruments as well as instruments for general surgery or as part of robotically controlled end effectors. These end effector mechanisms include multiple grasping elements paired with drive links. Each grasping element also serves as a stabilizing link for the next most distal grasping element, forcing it to maintain its relative angle with respect to the opposing grasping elements.

22 Claims, 31 Drawing Sheets

END EFFECTOR MECHANISM FOR A SURGICAL INSTRUMENT

CROSS REFERENCE TO RELATED CO-PENDING APPLICATIONS

This application claims the benefit of U.S. provisional application Ser. No. 60/895,760 filed on Mar. 20, 2007 and entitled IMPROVED END EFFECTOR MECHANISM FOR A SURGICAL INSTRUMENT which is commonly assigned and the contents of which are expressly incorporated herein by reference.

FIELD OF THE INVENTION

The present invention relates to an improved end effector mechanism for a surgical instrument, and more particularly to a multi-component end effector mechanism for a surgical instrument that provides grasping of large objects of any shape.

BACKGROUND OF THE INVENTION

End effector mechanisms refer to the portion of a surgical instrument that contacts and manipulates tissue in a patient. Prior art end effectors include grasping forceps, which grasp but do not intentionally cut or puncture tissue. These devices replace the surgeon's hands in the traditional open surgery. However, prior grasping devices often cause problems due to their inability to properly grasp an object. The lack of satisfactory holding power of these instruments can complicate the surgeon's work. Tissue that must be manipulated during a surgical procedure can have widely varying shapes or surface characteristics and can be highly slippery and difficult to grasp. Additionally, such prior devices lack the necessary holding power, thereby forcing the physician to exert significant grasping pressure in order to manipulate tissue as required to perform the surgical procedure. Use of such high grasping pressures can result in increased long-term trauma to the tissue.

Referring to FIG. 2, a typical surgical instrument 25 has a hollow cylindrical shaft 32, which includes a solid actuating rod (not shown). The rod is connected at the distal end to the effector mechanism 31 and at the proximal end to one member of the handle assembly 30. When the handle is operated, the rod slides through the shaft and actuates the end effector mechanism. Serrations and other features enable the end effector to perform various surgical functions, such as gripping or cutting.

Many creative linkages have been devised for converting the surgeon's manual efforts, at the handle end of the instrument, into opening and closing of the instrument's jaws. Typically, the handle assembly 30 has a stationary member 35 rigidly joined to a hollow shaft 32 and a movable member 34 pivotally joined (with pivot pin 33) to an actuator rod that is mounted and is capable of reciprocal movement within the shaft. When the surgeon squeezes the stationary and movable handle members together, the actuating rod acts upon the jaws in such a way as to make the jaws close. When the surgeon spreads the stationary and movable members apart, the movements are reversed and the jaws open.

In many prior art instruments the end effector mechanism 31 includes upper and a lower elongated jaw components 45, 46, pivotally connected to each other and to the shaft 32 and actuator rod with pivot pin 90. When operating the jaws 45, 46 of a typical instrument, surgeons have experienced difficulty in grasping slippery tissues because the jaws close first at their rear ends, and thereby tend to propel or push the tissues out from between the jaws, as illustrated in FIG. 1A. Consequently, trauma of the tissue may result from repeated and increasingly aggressive attempts to grasp the tissue.

U.S. Pat. No. 6,238,414 describes a surgical instrument that addresses the problem of grasping a large cylindrical object by keeping the opening jaws parallel to each other, as shown in FIG. 1B, FIG. 2A and FIG. 2B. However, this jaw arrangement is not always optimal for grasping a large object, especially one that is not cylindrically shaped. Accordingly, there is a need for improved end effector mechanisms that provide optimal grasping of large objects of any shape.

SUMMARY OF THE INVENTION

The present invention describes improved end effector mechanisms used in minimally invasive surgical instruments as well as instruments for general surgery or as part of robotically controlled end effectors.

In general, in one aspect, the invention features a surgical instrument comprising an improved end effector assembly. The improved end effector assembly includes a housing, a pivot driver disposed within the housing and configured to reciprocate longitudinally within the housing and first and second gripping members extending from the housing. The first gripping member includes a first jaw element, a second jaw element and a drive element. The first jaw element has a first end pivotally connected to a first location of the housing and a second end pivotally connected to a first location of a first end of the second jaw element. The drive element has a first end pivotally connected to a first location of the pivot driver and a second end pivotally connected to a second location of the first end of the second jaw element. The first housing location and the first pivot driver location are separated by an adjustable distance and by adjusting this distance any desired angular orientations between the first and second jaw elements is established.

Implementations of this aspect of the invention may include one or more of the following features. The surgical instrument further includes first actuation means for moving the first gripping member relative to the second gripping member. The first actuation means includes a first actuator rod configured to reciprocate longitudinally within the housing and the pivot driver. The first gripping member drive element rotatively engages a first location of a first end of the first actuator rod and linear motion of the first actuator rod translates into rotational motion of the first gripping member drive element and the rotational motion of the first gripping member drive element moves the first gripping member relative to the second gripping member. The surgical instrument further includes means for adjusting the distance between the first housing location and the first pivot driver location. The means for adjusting the distance between the first housing location and the first pivot driver location actuates longitudinal linear motion of the pivot driver and the linear motion of the pivot driver translates into rotational motion of the first gripping member drive element and the rotational motion of the first gripping member drive element moves the first gripping member second jaw element relative to the first gripping member first jaw element. The second gripping member includes a first jaw element, a second jaw element and a drive element. The second gripping member first jaw element has a first end pivotally connected to the first location of the housing and a second end pivotally connected to a first location of a first end of the second gripping member second jaw element. The second gripping member drive element has a first end pivotally connected to the first location of the pivot driver and a second end pivotally connected to a second location of the first end of the second gripping member second jaw element. The means for adjusting the distance between the first housing location and the first pivot driver location actuates longitudinal linear motion of the pivot driver and the linear motion of the pivot driver translates into rotational motion of the second gripping member drive element and the rotational motion of the second gripping member drive element moves the second gripping member second jaw element relative to the second gripping member first jaw element. The second gripping member drive element rotatively engages a second location of the first end of the first actuator rod and linear motion of the first actuator rod translates into rotational motion of the second gripping member drive element and the rotational motion of the second gripping member drive element moves the second gripping member relative to the first gripping member. The first actuation means may further comprise a second actuator rod configured to reciprocate longitudinally within the housing and the second gripping member drive element engages a first location of a first end of the second actuator rod. Linear motion of the second actuator rod translates into rotational motion of the second gripping member drive element and the rotational motion of the second gripping member drive element moves the second gripping member relative to the first gripping member. The first end of the first actuator rod may include first and second fingers extending from the first end, and the first and second fingers have first and second yoke pins for rotatively engaging first and second linking yokes of the first and second gripping member drive elements, respectively. The first ends of the first and second actuator rods comprise first and second yoke pins for rotatively engaging first and second linking yokes of the first and second gripping member drive elements, respectively. The pivot driver may be a hollow tube. The surgical instrument may further include a handle assembly for actuating the first actuation means and the means for adjusting the distance between the first housing location and the first pivot driver location. The surgical instrument may further include a shaft assembly comprising a hollow sheath, the first actuation means and the means for adjusting the distance between the first housing location and the first pivot driver location. The first gripping member may further comprise a third jaw element and a second drive element and the third jaw element comprises a first end pivotally connected to a first location of the second end of the second jaw element, and the second drive element comprises a first end pivotally connected to a second location of the first end of the second jaw element and a second end pivotally connected to a second location of the first end of the third jaw element. The surgical instrument may further include additional jaw elements and additional drive elements for each of the first and second gripping members. The jaw elements may have inner surfaces comprising one of serrations, aggressive teeth, atraumatic teeth, an elbow, or protrusions. The gripping members may be disposable. The second gripping member may be fixedly connected to the housing. The end effector assembly may be robotically controlled. The end effector assembly may be used in minimally invasive surgery.

In general, in another aspect, the invention features a prosthetic assembly comprising the improved end effector assembly, as was described above. In another aspect, the invention features a robotic assembly comprising an improved end effector assembly, as was described above.

In yet another aspect, the invention features a method for setting any desired angular orientation between first and second jaw elements of a first gripping member of an end effector assembly. The method includes providing a housing, providing a pivot driver disposed within the housing and configured to reciprocate longitudinally within the housing and providing the first gripping member and a second gripping member. The first gripping member comprises the first and second jaw elements and a drive element. Next, pivotally connecting a first end of the first jaw element to a first location of the housing and a second end of the first jaw element to a first location of a first end of the second jaw element. Next, pivotally connecting a first end of the drive element to a first location of the pivot driver and a second end of the drive element to a second location of the first end of the second jaw element. The first housing location and the first pivot driver location are separated by an adjustable distance. Next, providing means for adjusting the distance between the first housing location and the first pivot driver location and adjusting the distance between the first housing location and the first pivot driver location thereby establishing any desired angular orientations between the first and second jaw elements.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views.

DETAILED DESCRIPTION OF THE INVENTION

Figure 5A:
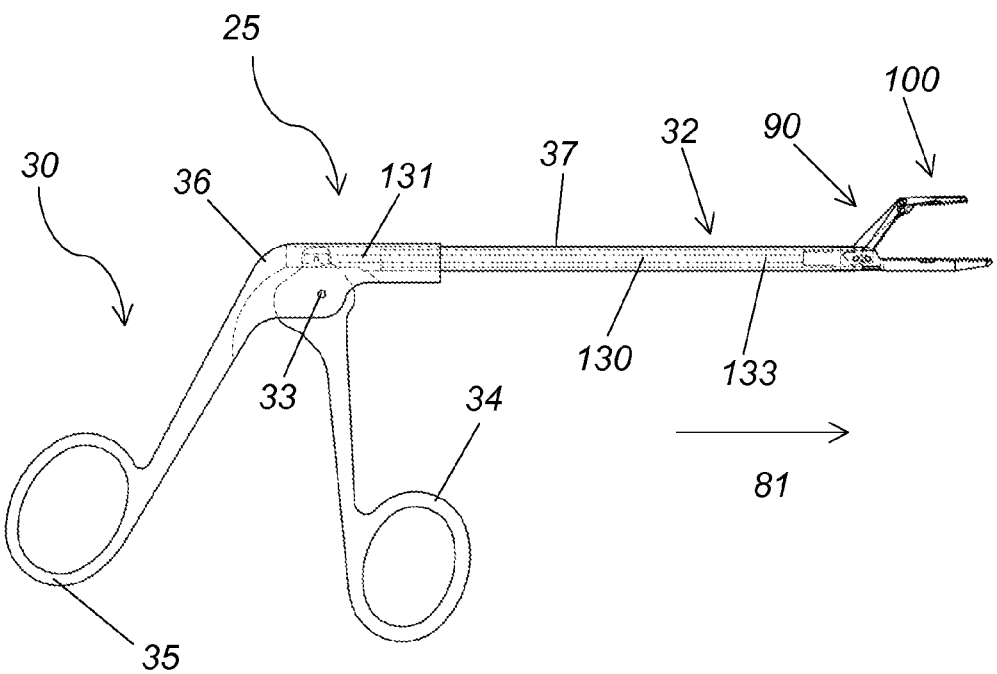
FIG. 5A is a side view of a surgical instrument with the end effector mechanism of FIG. 3.
Figure 5B:
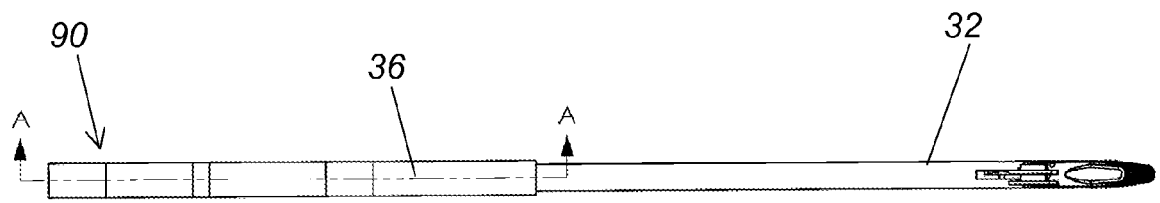
FIG. 5B a top view of the surgical instrument of FIG. 5A.
Figure 6:
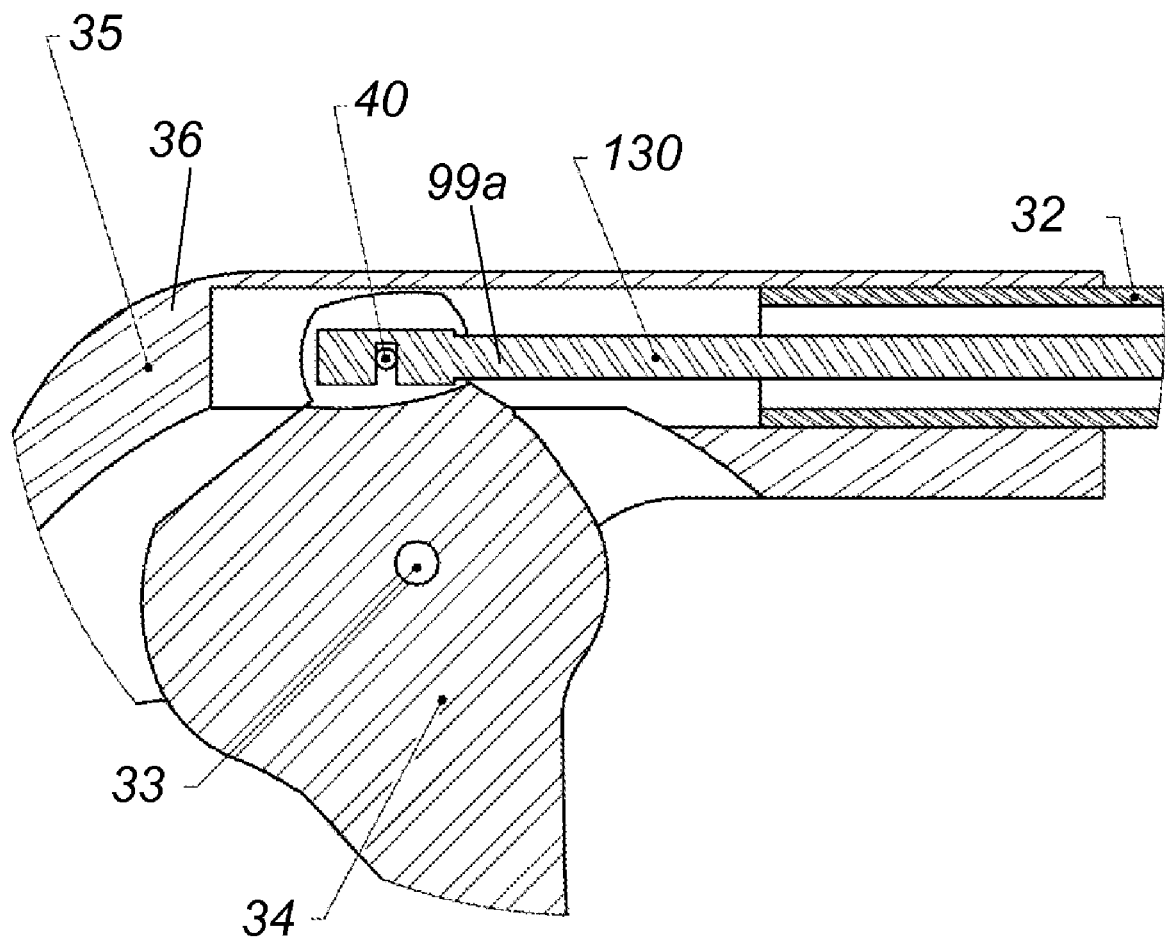
FIG. 6 is a partial cross sectional view of FIG. 5B along line A-A.

Referring to FIG. 5A and FIG. 5B, a surgical instrument 25 includes a front end assembly 90 with an end effector mechanism 100 and a handle assembly 30. The handle assembly 30 includes a stationary handle 35 and a movable handle 34 pivotally connected to the stationary handle 35 with pivot pin 33. Stationary handle 35 terminates in an upper barrel portion 36, which is substantially hollow and is connected to a distally extending shaft assembly 32. The shaft assembly 32 includes an outer hollow sheath 37 and a solid coaxial internal actuation rod 130. Actuation rod 130 has a first end 99a connected to the movable handle 34 with drive pin 40, shown in FIG. 6, and reciprocates coaxially within the hollow sheath 37 in response to manipulation of the movable handle 34 by the user. Actuation rod 130 has a second end 99b connected to actuator 132 which in turn is connected to the end effector mechanism 100, shown in FIG. 7. Actuator rod 130 translates the motion of the movable handle 34 into a motion of the end effector mechanism 100. Actuator 132 has an elongated body 133, an upper finger 134 and a lower finger 136. An opening 138 is formed between upper finger 134 and lower finger 136. Upper finger 134 also includes a yoke pin 135 extending from an outer surface of finger 134. In one example, actuator 132 connects to actuator rod 130 according to a method described in U.S. Pat. No. 6,238,414, the contents of which are incorporated herein by reference.

Figure 1A:
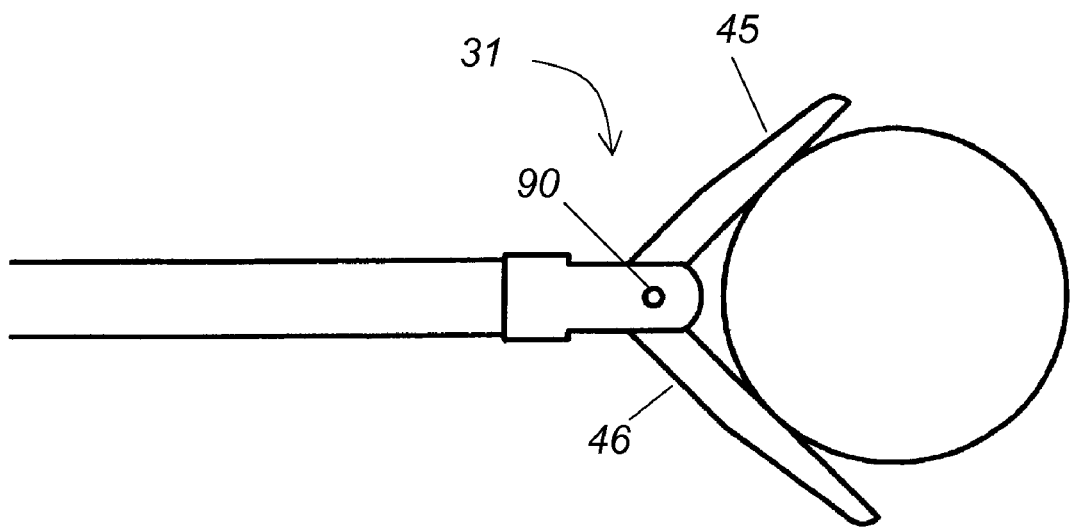
FIG. 1A is a schematic diagram of a typical prior art end effector mechanism.
Figure 1B:
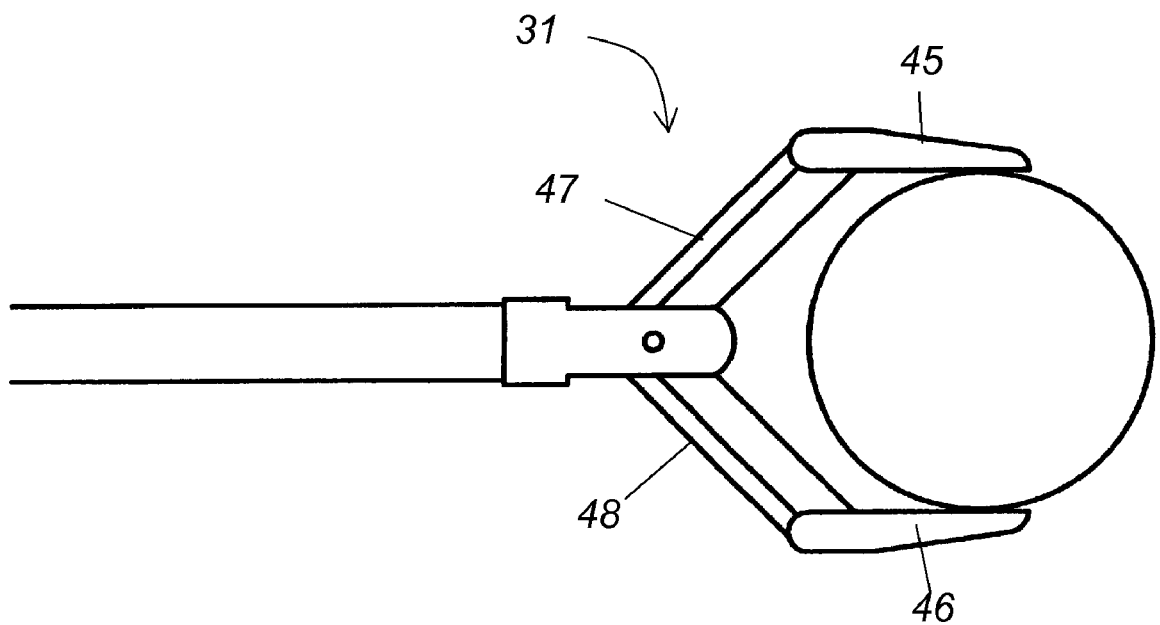
FIG. 1B is a schematic diagram of a prior art end effector mechanism with parallel jaw elements.
Figure 2A:
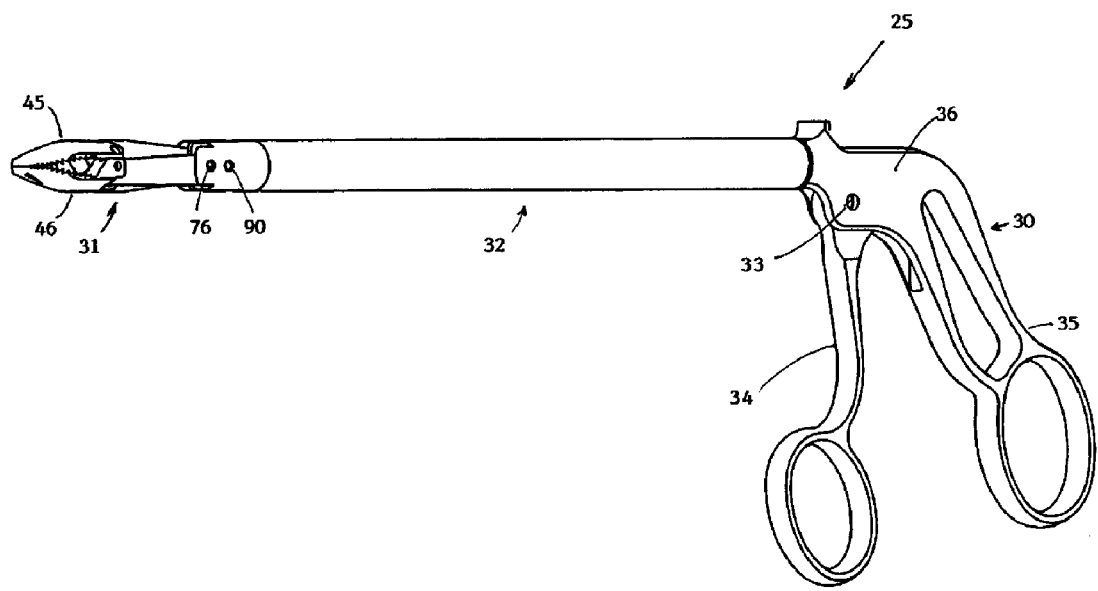
FIG. 2A is a perspective view of a surgical instrument with the end effector mechanism of FIG. 1B with the parallel jaws closed.
Figure 2B:
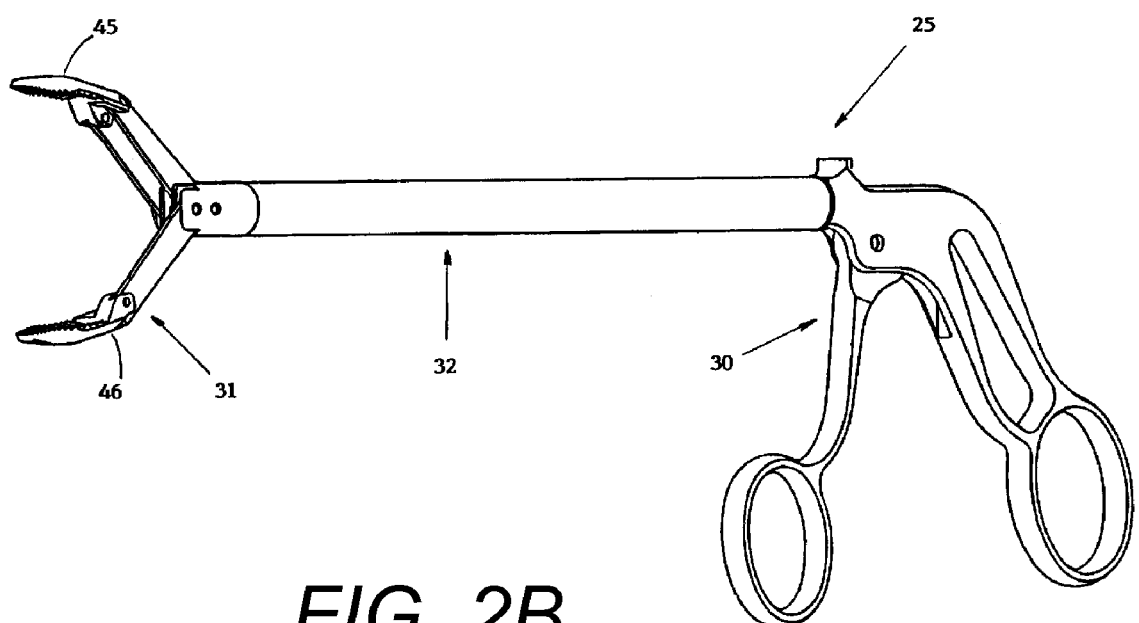
FIG. 2B is a perspective view of a surgical instrument with the end effector mechanism of FIG. 1B with the parallel jaws open.
Figure 3:
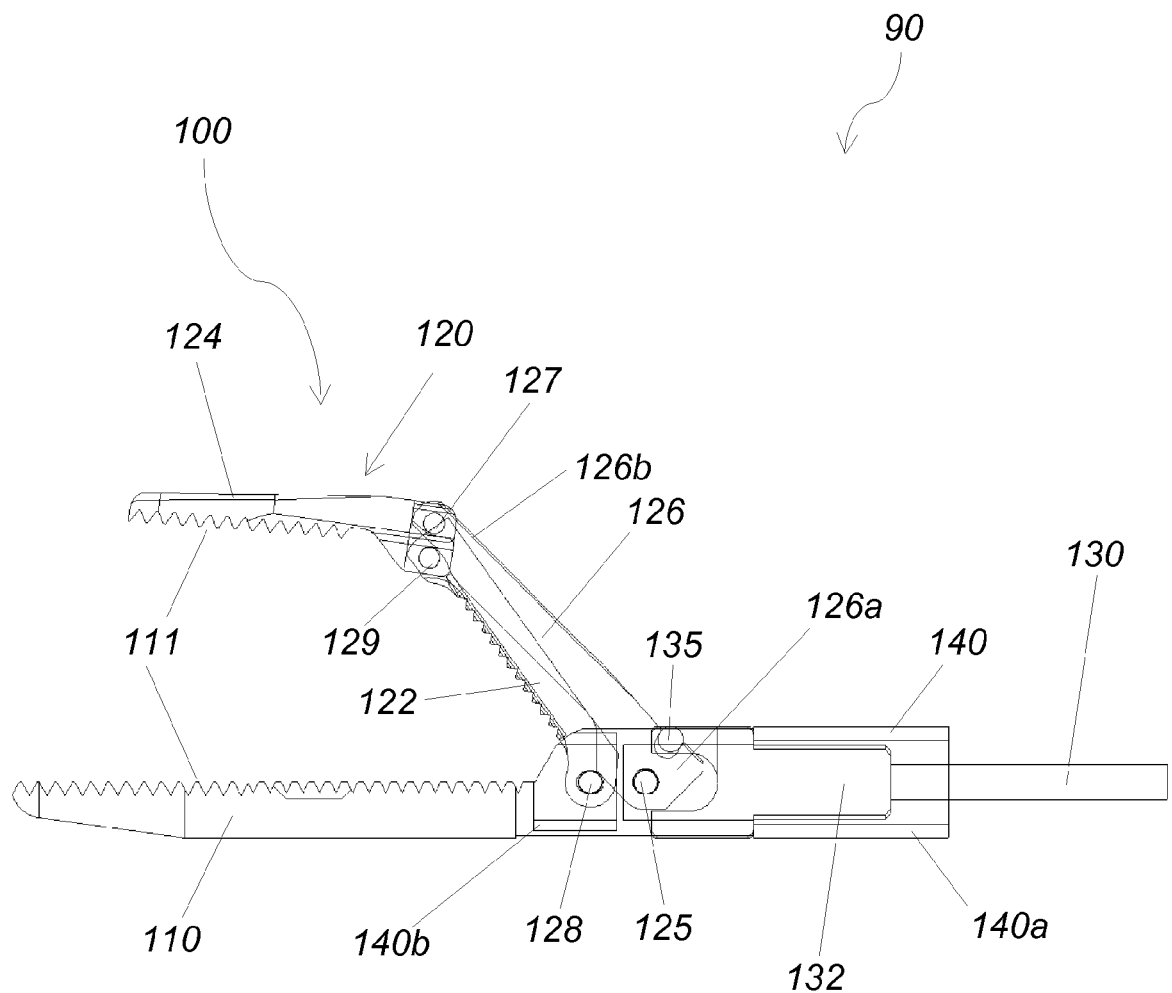
FIG. 3 is a transparent side view of a first embodiment of an improved end effector mechanism.
Figure 4A:
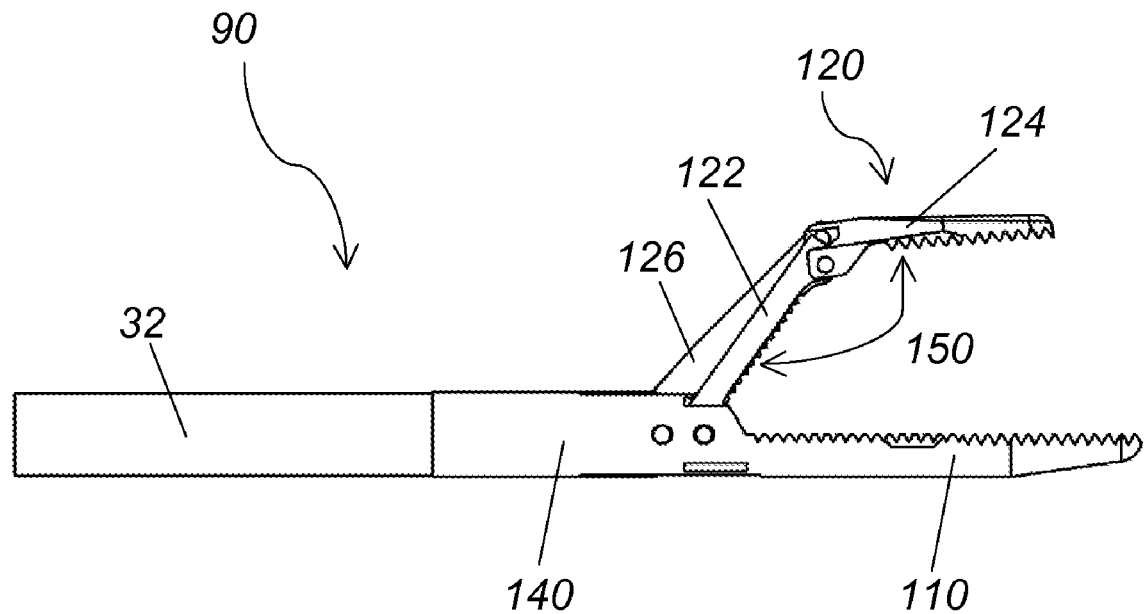
FIG. 4A is a side view of the first embodiment of FIG. 3 with the top jaw open.
Figure 4B:
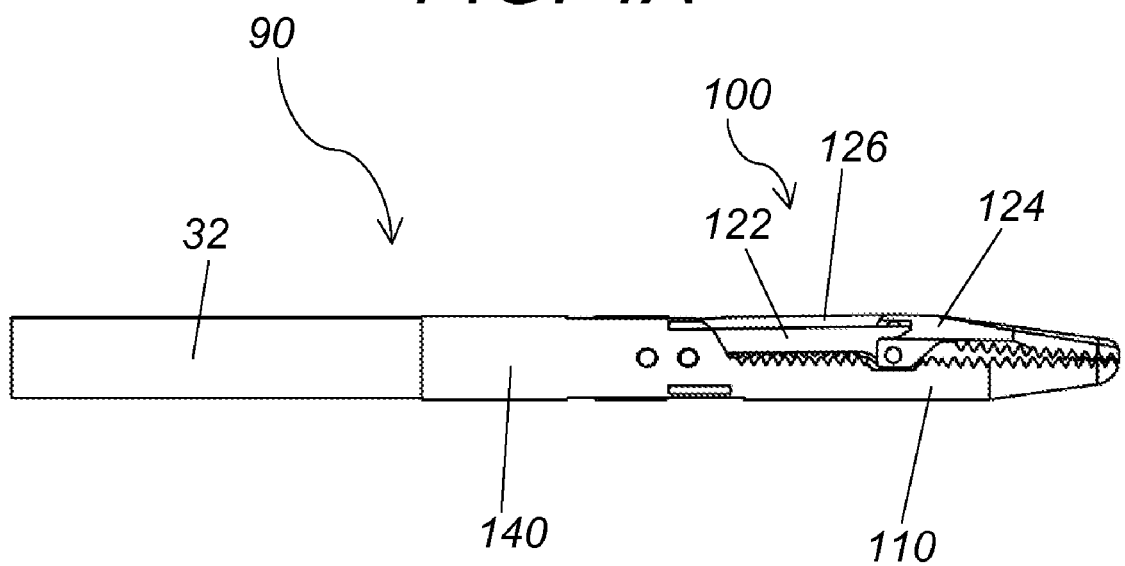
FIG. 4B is a side view of the first embodiment of FIG. 3 with the top jaw closed.
Figure 7:
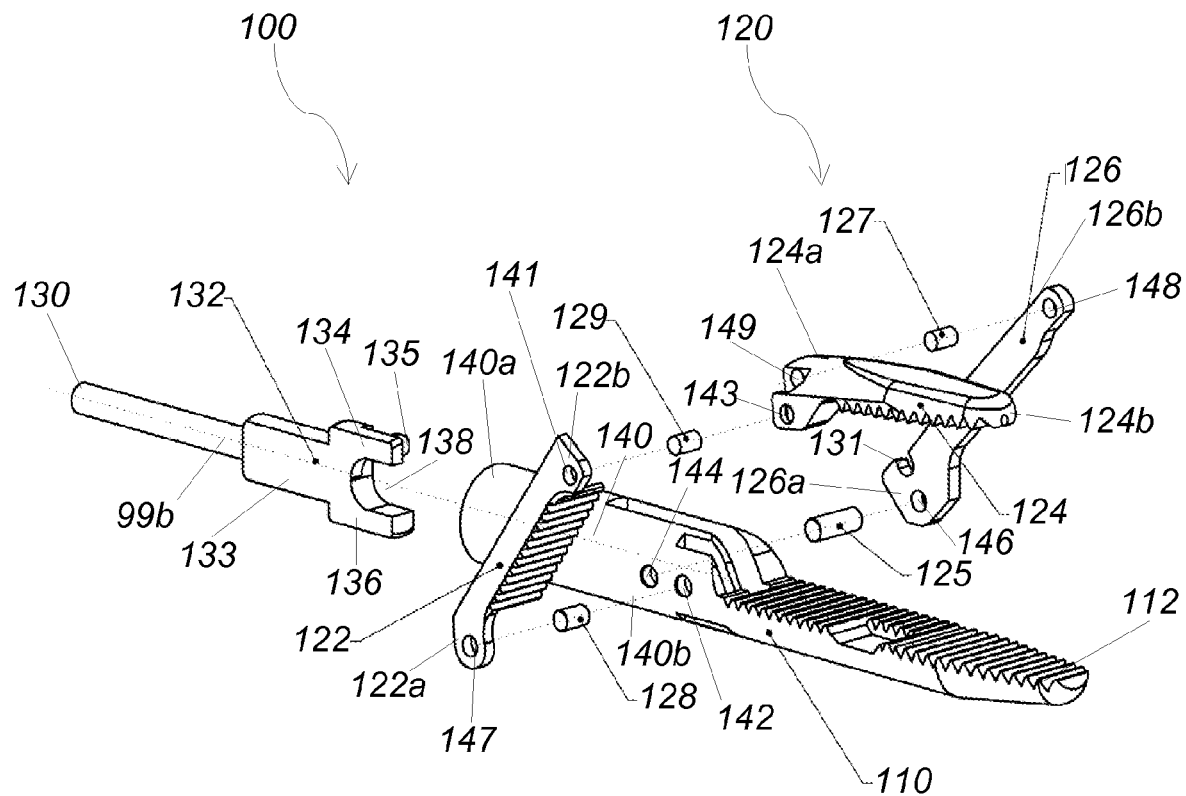
FIG. 7 is an exploded view of the end effector mechanism of FIG. 3.

Referring to FIG. 3 and FIG. 7, a first embodiment of an end effector assembly 90 includes a housing 140 and the end effector mechanism 100. Housing 140 includes a hollow tube having one end 140a connected to a distal end of the outer hollow sheath 37 and a second end 140b connected to the end effector mechanism 100. Housing end 140b also includes through openings 142, 144. Actuator 132 is disposed within housing 140. End effector mechanism 100 includes a stationary jaw 110 extending longitudinally from the second end 140b of housing 140 and a movable jaw 120 pivotally connected to the second end 140b of housing 140. Movable jaw 120 includes a first jaw element 122, second jaw element 124 and drive element 126. Drive element 126 has one end 126a pivotally connected to the second end 140b of housing 140 by inserting pivot pin 125 into through-opening 144 of the housing 140 and through-opening 146 of the drive element 126. A second end 126b of the drive element 126 is pivotally connected to a first end 124a of the second jaw element 124 by inserting pivot pin 127 into through-opening 148 of the drive element 126 and through-opening 149 of the second jaw element 124. End 126a of drive element 126 also includes a linking yoke 131 configured to rotatively engage a yoke pin 135 extending from the upper finger 134 of actuator 132. First jaw element 122 has a first end 122a pivotally connected to housing end 140b by inserting pivot pin 128 into through-opening 147 of the first jaw element 122 and into through-opening 142 of the housing 140. A second end 122b of the first jaw element 122 is pivotally connected to the first end 124a of the second jaw element 124 by inserting pivot pin 129 into through-openings 141 and 143 of the first jaw element 122 and second jaw element 124, respectively. First and second jaw elements 122, 124 and stationary jaw 110 have flat inner surfaces with rounded edges suitable for grasping an organ or tissue without damaging them. The inner surfaces of the stationary jaw 110, first jaw element 122 and second jaw element 124 may also include atraumatic serrations or teeth 111 suitable for grasping an organ or tissue. As was mentioned above, end 126a of drive element 126 is rotatively connected to the actuator upper finger 134 via the linking yoke 131 engaging the yoke pin 135 and thereby the forward linear motion of the actuator rod 130 is translated into mainly downward rotating motion of the drive element 126. The downward rotating motion of the drive element 126 causes the first end 124a of the second jaw element 124 and the thereto pivotally connected second end 122b of the first jaw element 122 to pivot downward, thereby closing the first and second jaw elements 122, 124 relative to the stationary jaw 110, as shown in FIG. 4B. Similarly, the backward linear motion of the actuator rod 130 is translated into mainly upward rotating motion of the drive element 126 and the upward rotating motion of the drive element 126 causes the first and second jaw elements 122, 124 to open relative to the stationary jaw 110, as shown in FIG. 4A. The angle 150 between the first and second jaw elements 122, 124 depends upon the geometric location of pivot holes 142 and 144 relative to each other, which in this embodiment is fixed. In this embodiment, the distance between pivot holes 142 and 144 and the corresponding pivot pins 125 and 128 is such that the inner surface of the second jaw 124 is arranged parallel to the inner surface of the stationary jaw 110.

Referring to the embodiment of FIG. 28-FIG. 31, jaw 110 is also movable and comprises a first jaw element 112, second jaw element 114 and drive element 116. Drive element 116 has one end 116a pivotally connected to the second end 140b of housing 140 by inserting pivot pin 125 into through-opening 144 of the housing 140 and through-opening 146b of the drive element 116. A second end 116b of the drive element 116 is pivotally connected to a first end 114a of the second jaw element 114 by inserting pivot pin 127b into through-opening 148b of the drive element 116 and through-opening 149b of the second jaw element 114. End 116a of drive element 116 also includes a linking yoke 131b configured to rotatively engage a yoke pin 137 extending from the lower finger 136 of actuator 132. First jaw element 112 has a first end 112a pivotally connected to housing end 140b by inserting pivot pin 128 into through-opening 147b of the first jaw element 112 and into through-opening 142 of the housing 140. A second end 112b of the first jaw element 112 is pivotally connected to the first end 114a of the second jaw element 114 by inserting pivot pin 129b into through-openings 141b and 143b of the first jaw element 112 and second jaw element 114, respectively.

Figure 8:
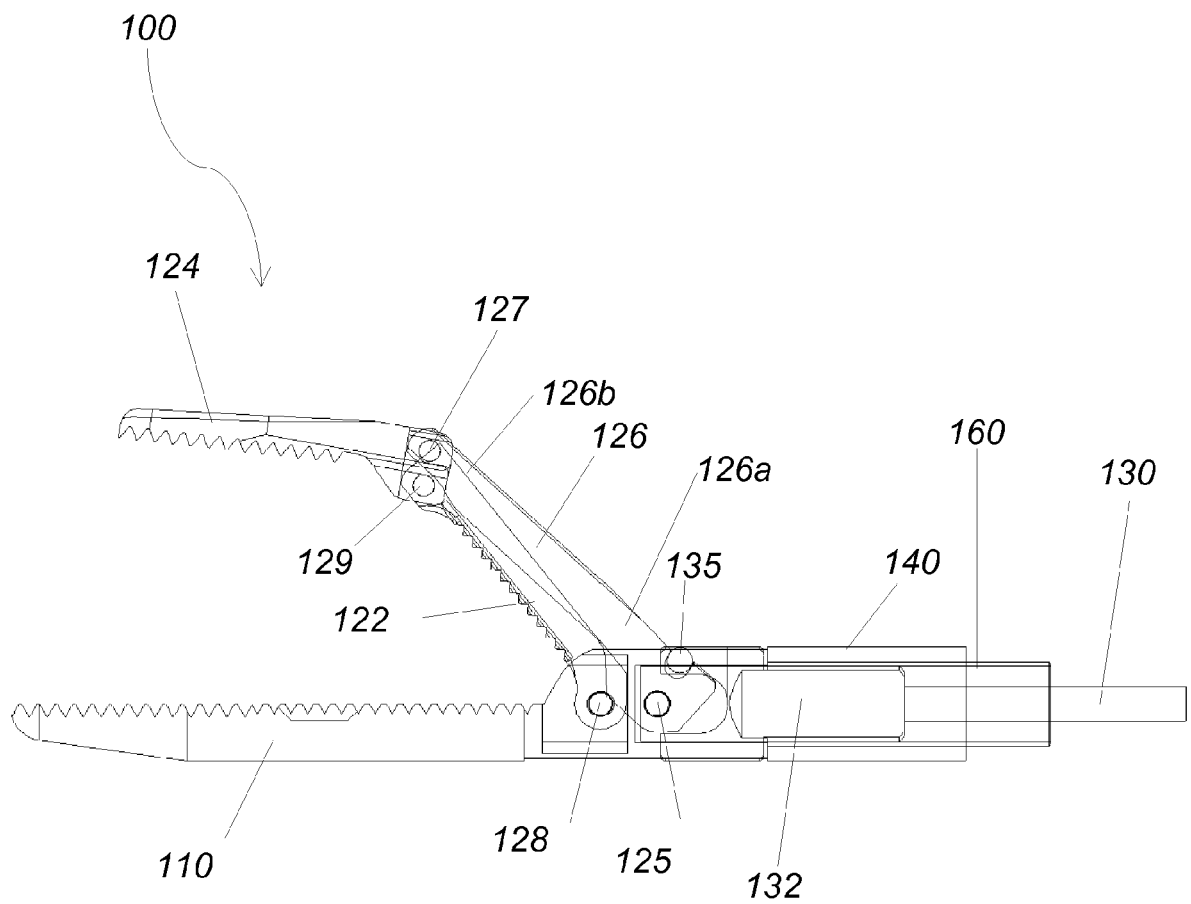
FIG. 8 is a transparent side view of a second embodiment of an improved end effector mechanism.
Figure 9A:
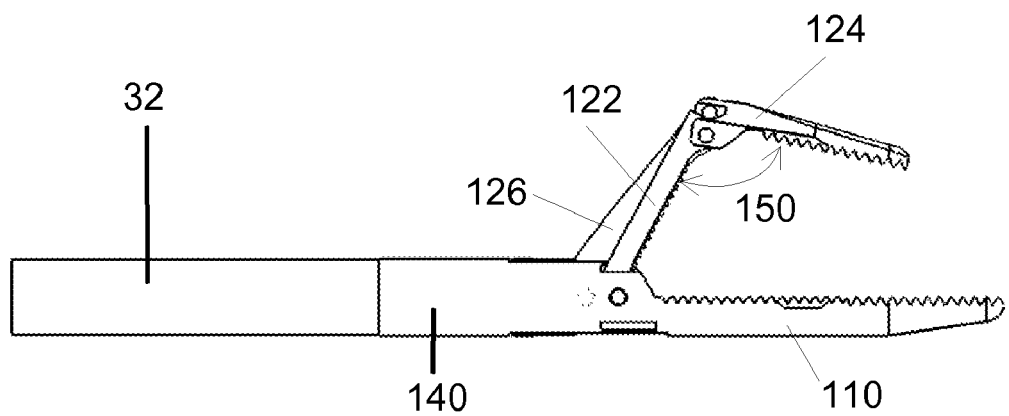
FIG. 9A is a side view of the end effector mechanism of FIG. 8 with the top jaw open forming a first angle with the lower stationary jaw.
Figure 9B:
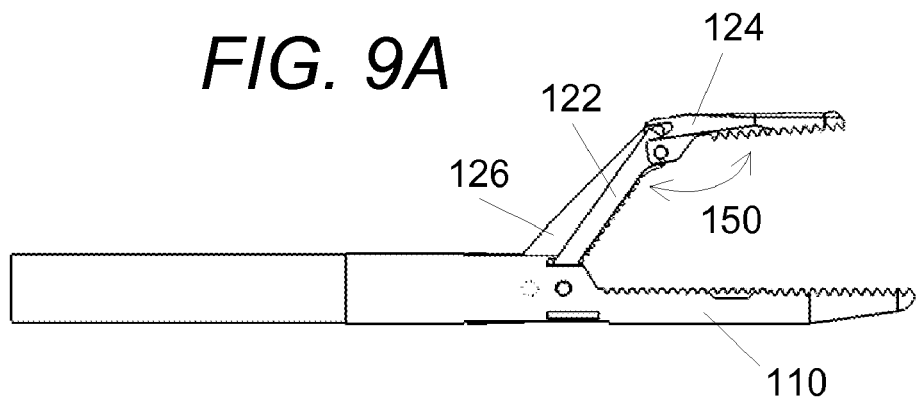
FIG. 9B is a side view of the end effector mechanism of FIG. 8 with the top jaw open forming a second angle with the lower stationary jaw.
Figure 9C:
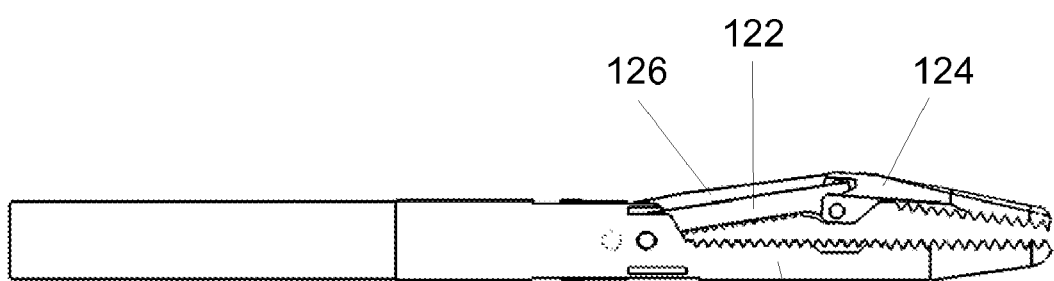
FIG. 9C is a side view of the end effector mechanism of FIG. 8 with the top jaw partially closed relative to the lower stationary jaw.
Figure 9D:
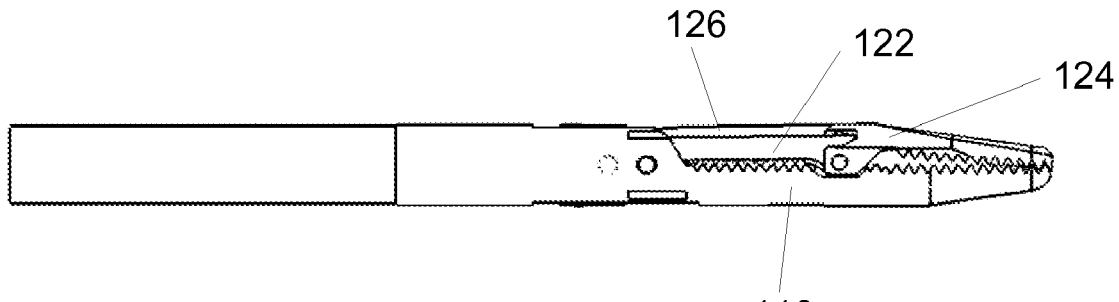
FIG. 9D a side view of the end effector mechanism of FIG. 8 with the top jaw closed relative to the lower stationary jaw.
Figure 10B:
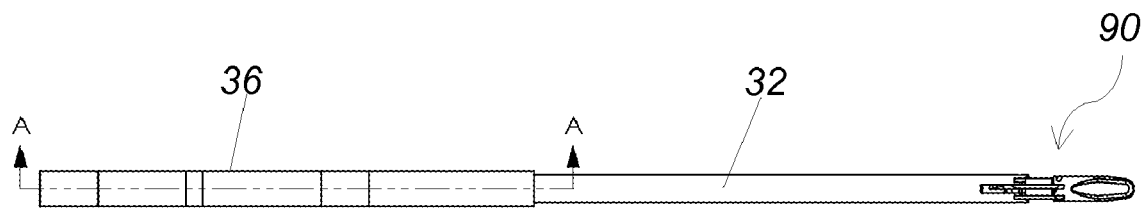
FIG. 10B a top view of the surgical instrument of FIG. 10A.
Figure 10A:
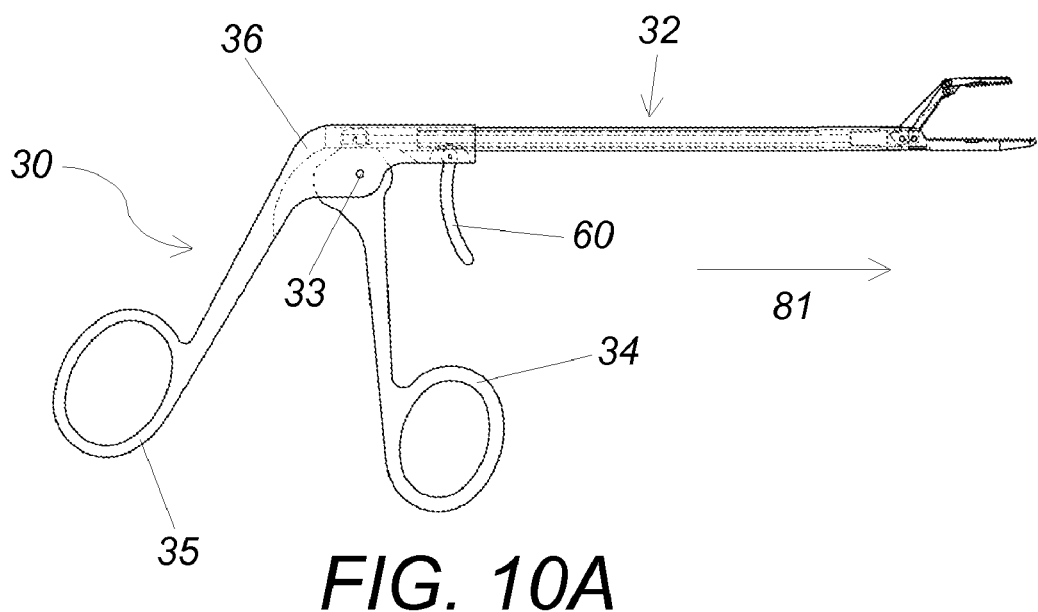
FIG. 10A is a side view of a surgical instrument with the end effector mechanism of FIG. 8.
Figure 10C:
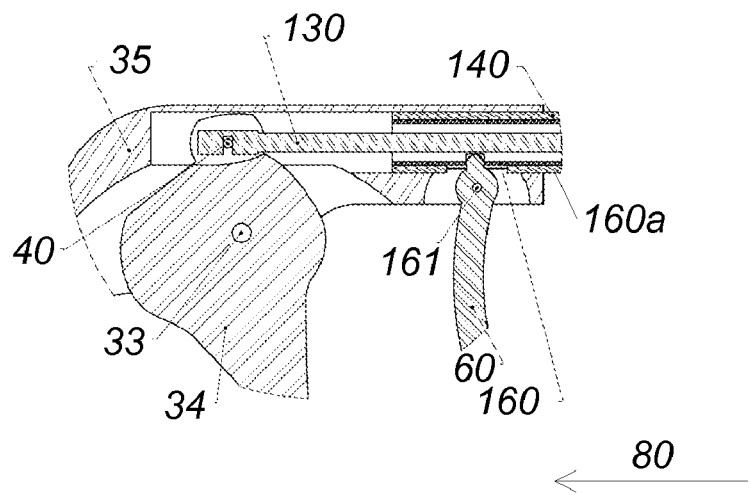
FIG. 10C is a partial cross sectional view of FIG. 10B along line A-A.
Figure 11:
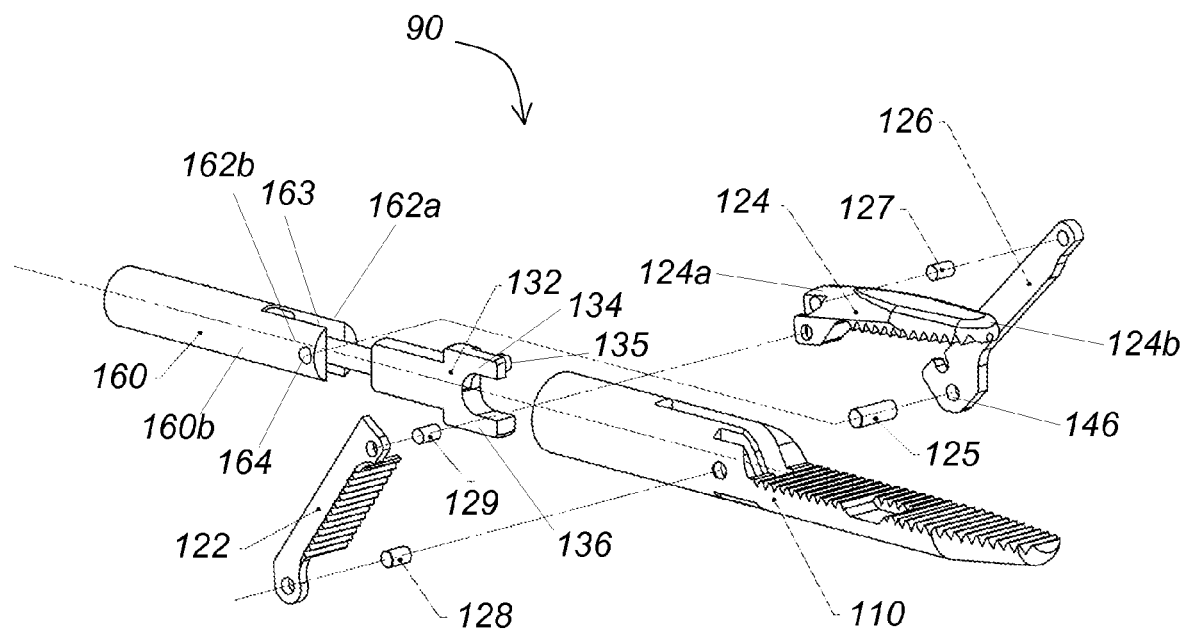
FIG. 11 is an exploded view of the end effector mechanism of FIG. 8.

Referring to FIG. 8 and FIG. 11, in a second embodiment of the end effector mechanism 100, the position of the pivot pins 125 and 128 relative to each other is variable and accordingly the angle 150 between the first and second jaw elements 122, 124 is varied thereby allowing any type of arrangement of the inner surface of the second jaw element 124 relative to the inner surface of the stationary jaw element 110, as shown in FIG. 9A-FIG. 9D. In this second embodiment, drive element 126 controls the opening and closing of the first jaw element 122 and a second driver 160 controls the orientation of the second jaw element 124 relative to the first jaw element 122, independently from the drive element 126. As shown in FIG. 8 and FIG. 11, the end effector assembly 90 of this embodiment includes a pivot driver 160, in addition to the housing 140 and the end effector mechanism 100. Referring to FIG. 10C, pivot driver 160 comprises a hollow tube disposed within housing 140 and is configured to house the actuator rod 130. A lever 60 is pivotally connected to a first end 160a of the pivot driver 160 with pivot pin 161. Moving the lever 60 backwards in the direction of arrow 80 causes the pivot driver 160 to move forward in the direction opposite to arrow 80. A second end 160b of pivot driver 160 includes flanges 162a, 162b and a through-opening 164 formed in flange 162b. Flange 162b is pivotally connected to drive element 126 by inserting pin 125 into through-opening 164 of flange 162b and through-opening 146 of the drive element 126. Moving pivot driver 160 forward causes pivot pin 125 to move closer to pivot pin 128 and drive element 126 to move further upward. Since the second end 126b of drive element 126 is pivotally connected to the first end 124a second jaw element 124 with pivot pin 127, the forward motion of pivot pin 125 causes the first end 124a of jaw element 124 to also move upward and the second end 124b of the jaw element 24 to move downward. In this way the orientation of the second jaw element 124 is initially set by the motion of the movable handle 34 through the actuator rod 130 and then further controlled by the motion of the lever 60 through the pivot driver 160.

Figure 12:
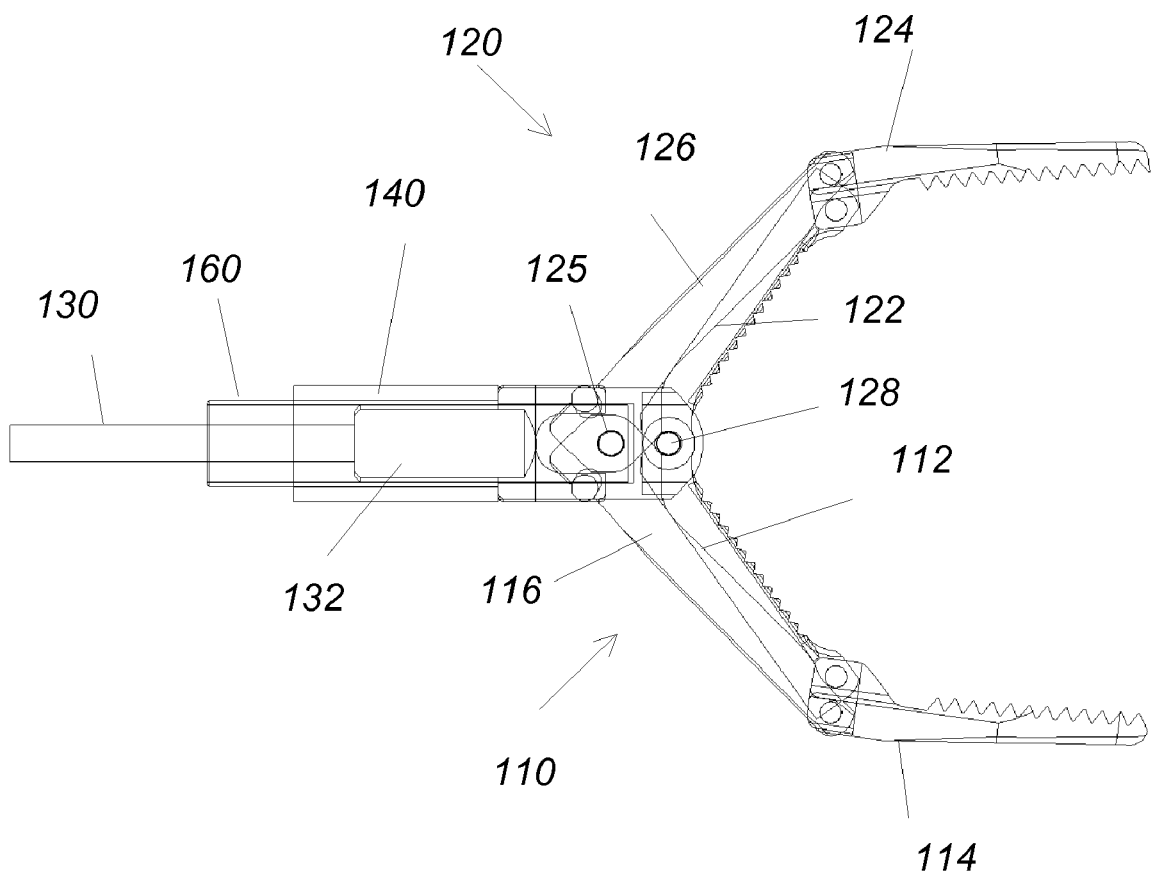
FIG. 12 is a transparent side view of a third embodiment of an improved end effector mechanism.
Figure 13A:
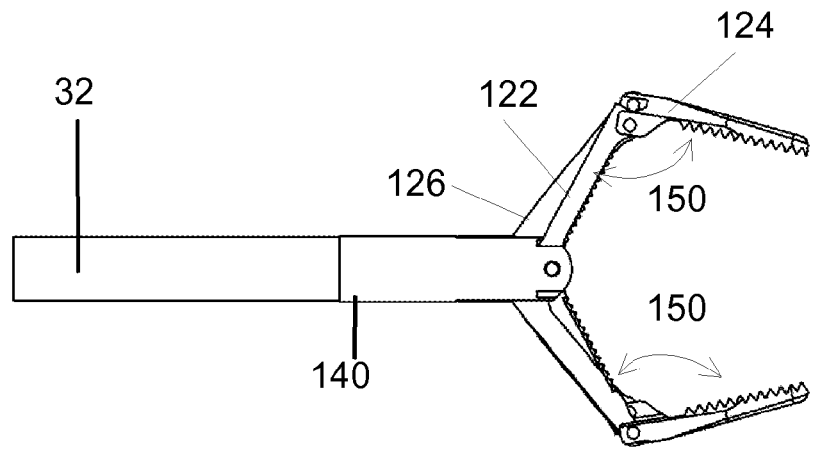
FIG. 13A is a side view of the end effector mechanism of FIG. 12 with the top jaw open forming a first angle with the lower jaw.
Figure 13B:
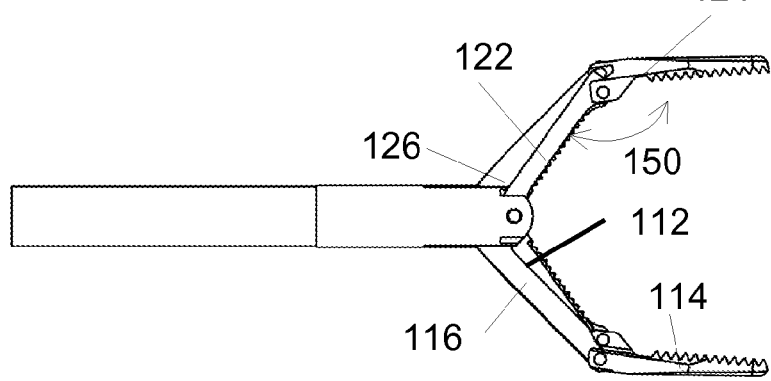
FIG. 13B is a side view of the end effector mechanism of FIG. 12 with the top jaw open forming a second angle with the lower jaw.
Figure 13C:
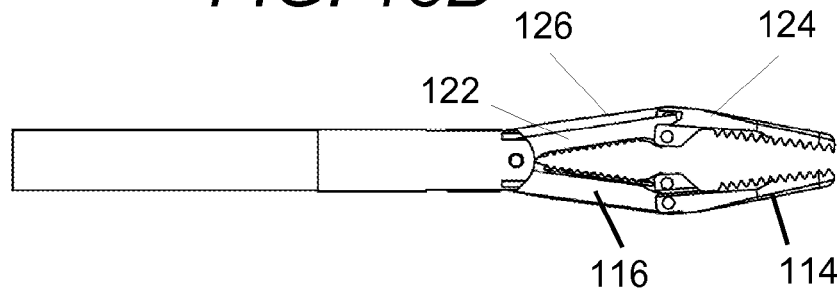
FIG. 13C is a side view of the end effector mechanism of FIG. 12 with the top jaw partially closed relative to the lower jaw.
Figure 13D:
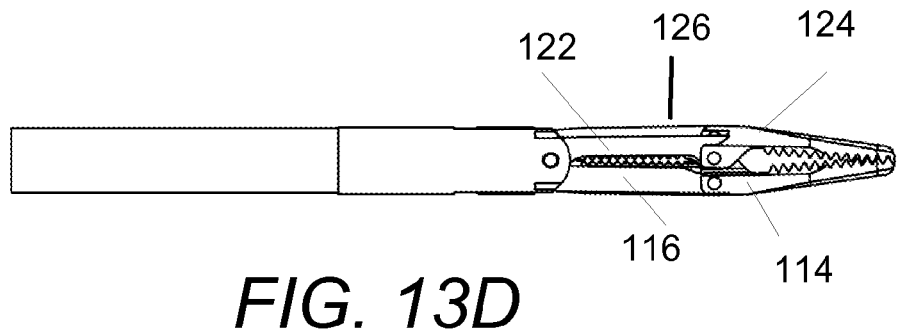
FIG. 13D a side view of the end effector mechanism of FIG. 12 with the top jaw closed relative to the lower jaw.
Figure 14:
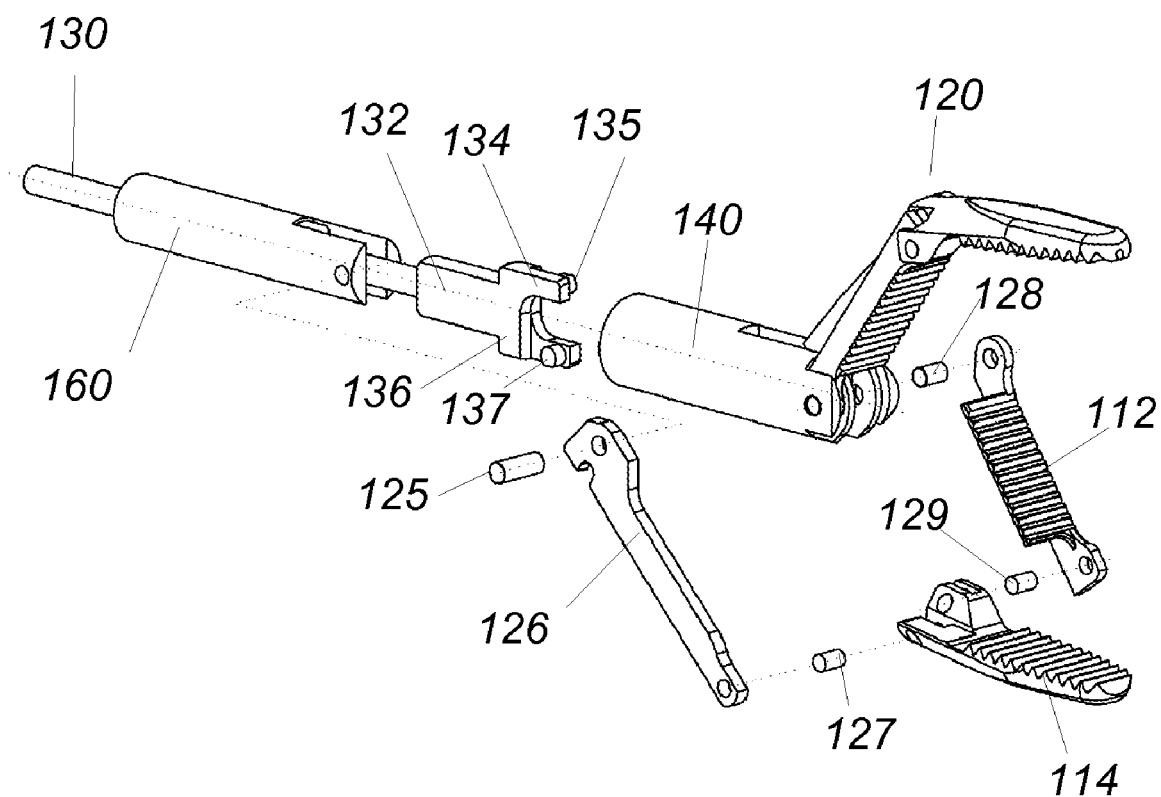
FIG. 14 is an exploded view of the end effector mechanism of FIG. 12.

Referring to FIG. 12 and FIG. 14 a third embodiment of the end effector mechanism 100, includes first and second sets of movable jaws 110, 120. First set of movable jaws 110 includes first and second jaw elements 112, 114 and drive element 116. Second set of movable jaws 120 includes first and second jaw elements 122, 124 and drive element 126. Both drive elements 116, 126 are actuated with one actuation rod 130 that reciprocates coaxially within the hollow sheath 37 in response to manipulation of the movable handle 34 by the user. Moving the handle 34 away from the stationary handle 35 pushes the actuator rod 132 backward in the direction of 80, shown in FIG. 10C and this backward motion of the actuator rod 132 causes the drive elements 116, 126 to rotate downward and upward, respectively, thereby opening the first and second movable jaw sets 110, 120. The location of pivot pin 125 connecting drive elements 116, 126 to the housing 140 is varied by an additional pivot driver mechanism 160, as was described above. This additional pivot drive mechanism 160 allows the second jaw elements 114, 124 to move relative to the corresponding first jaw elements 112, 122 for each jaw set 110, 120. FIG. 13A-FIG. 13D depict several positions of the two movable jaw sets 110, 120 relative to each other and the corresponding jaw elements relative to each other. In this embodiment jaw sets 110, 120 move symmetrically to each other.

Figure 15:
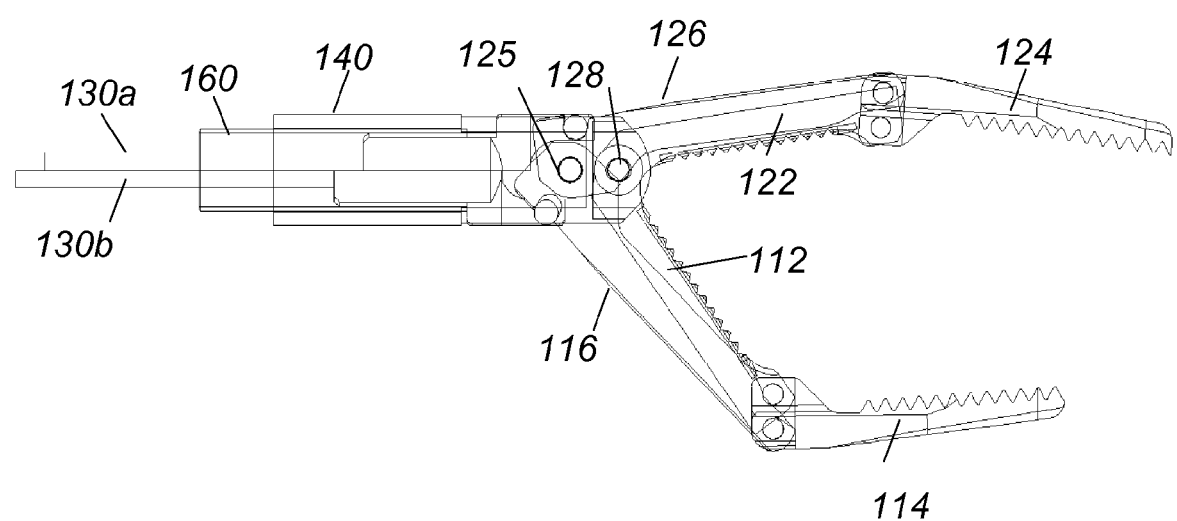
FIG. 15 is a transparent side view of a fourth embodiment of an improved end effector mechanism.
Figure 16A:
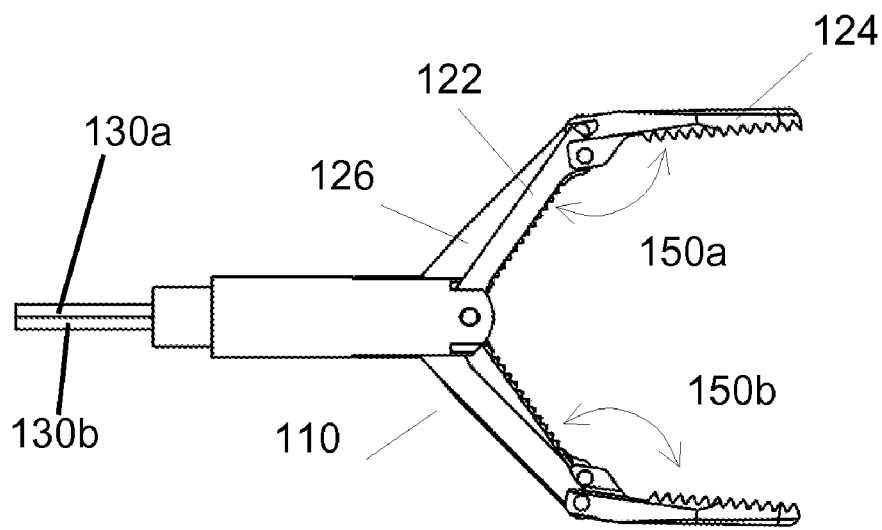
FIG. 16A is a side view of the end effector mechanism of FIG. 15 with the top jaw open forming a first angle with the lower jaw.
Figure 16B:
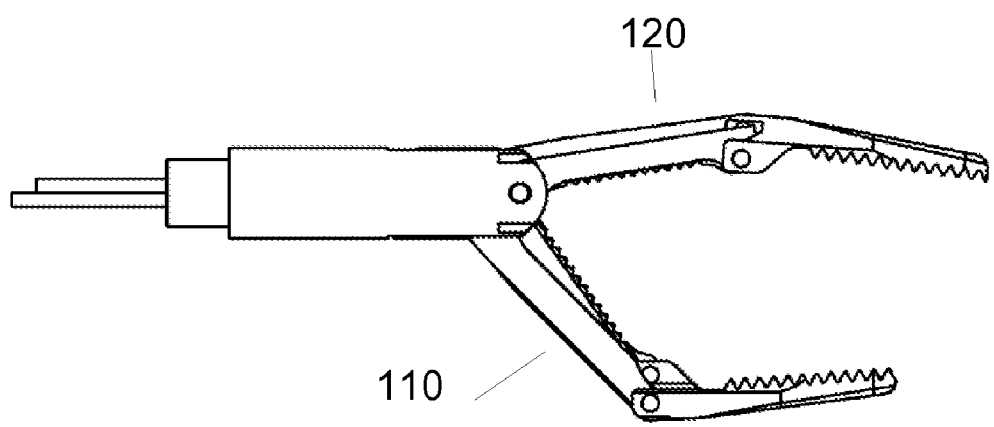
FIG. 16B is a side view of the end effector mechanism of FIG. 15 with the top jaw open forming a second angle with the lower jaw.
Figure 16C:
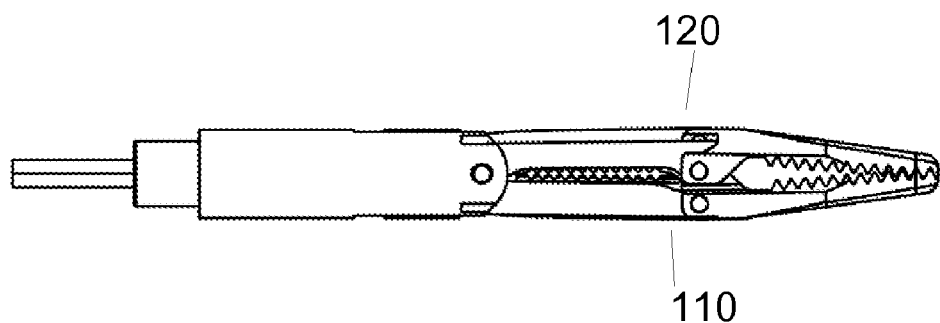
FIG. 16C is a side view of the end effector mechanism of FIG. 15 with the top jaw closed relative to the lower jaw.
Figure 17:
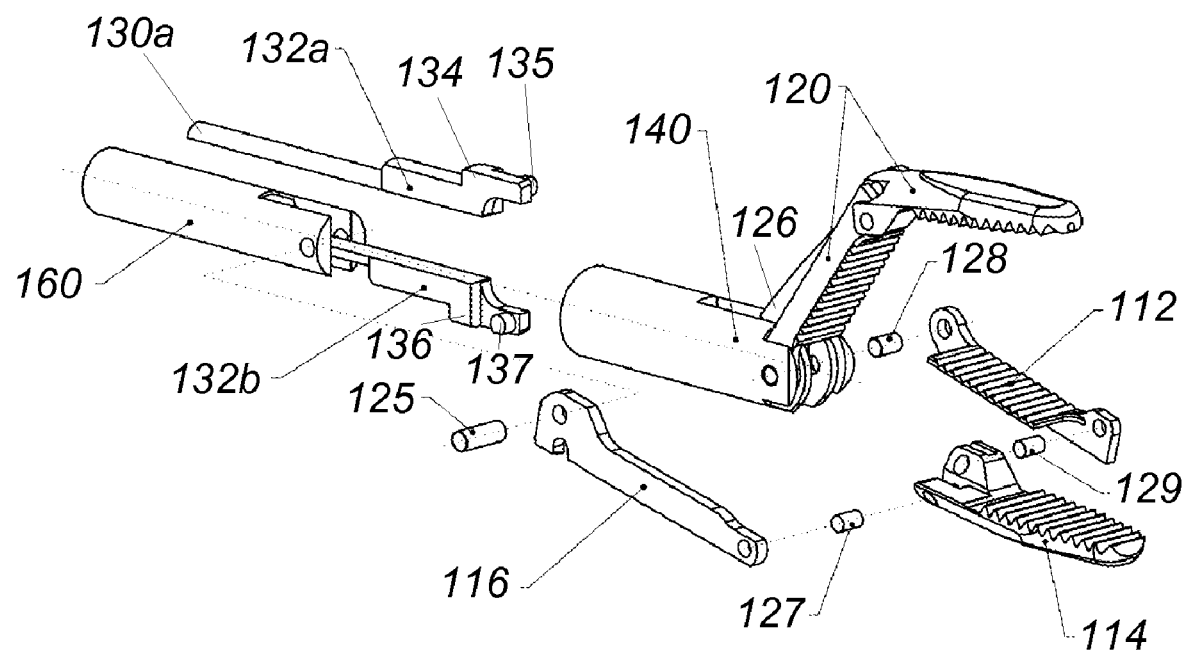
FIG. 17 is an exploded view of the end effector mechanism of FIG. 15.
Figure 18A:
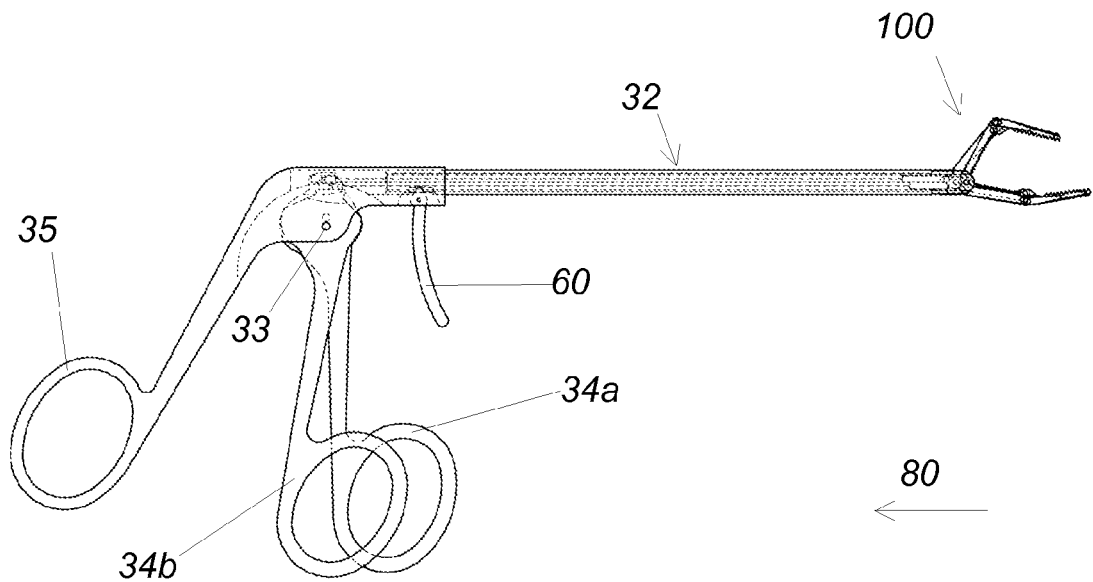
FIG. 18A is a side view of a surgical instrument with the end effector mechanism of FIG. 15.
Figure 18B:
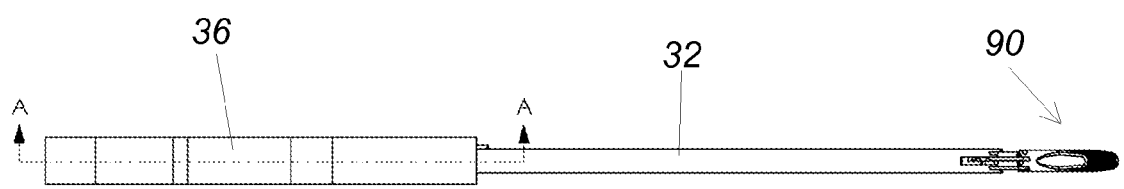
FIG. 18B a top view of the surgical instrument of FIG. 18A.
Figure 19:
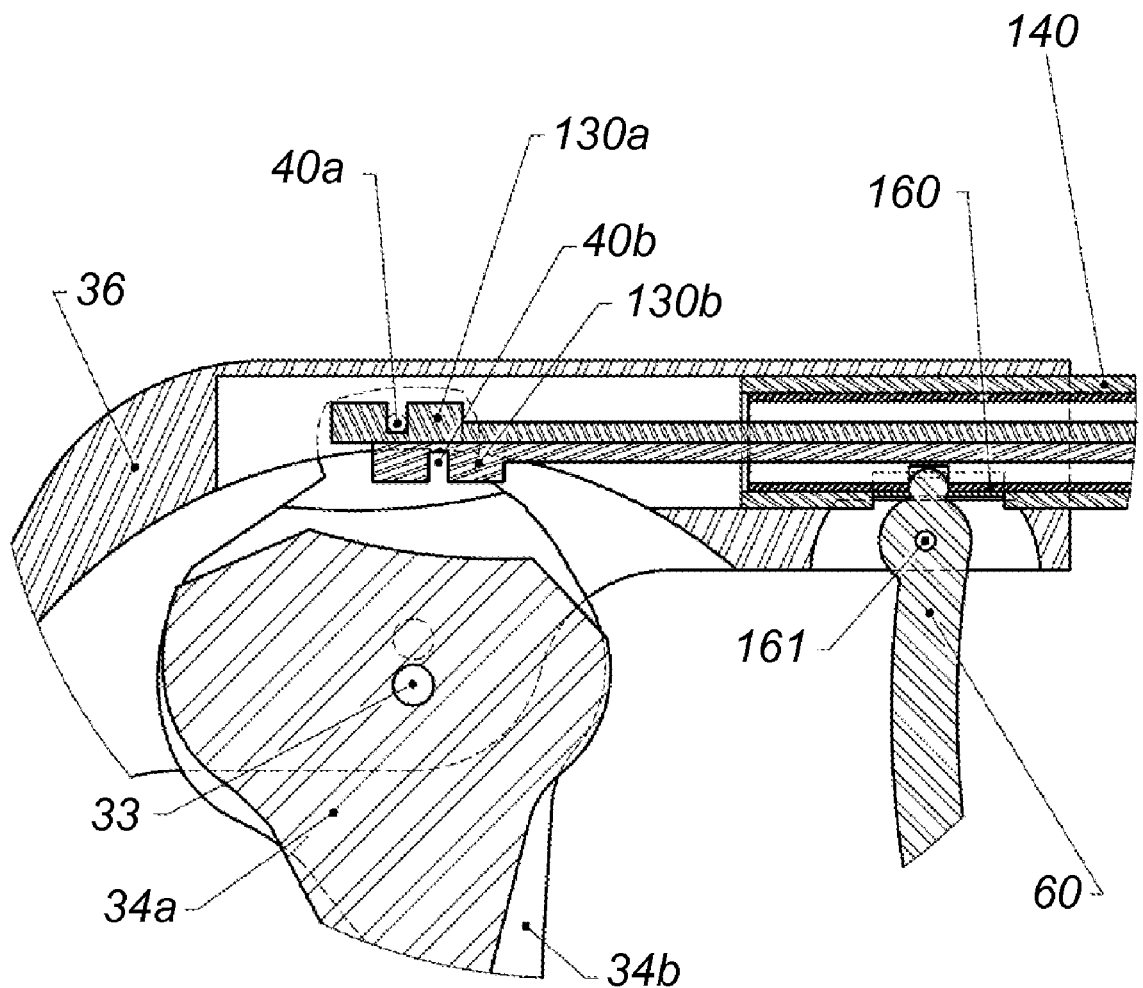
FIG. 19 is a partial cross sectional view of FIG. 18B along line A-A.

Referring to FIG. 15 and FIG. 17 a fourth embodiment of the end effector mechanism 100, includes first and second sets of movable jaws 110, 120. First set of movable jaws 110 includes first and second jaw elements 112, 114 and drive element 116. Second set of movable jaws 120 includes first and second jaw elements 122, 124 and drive element 126. Drive elements 116, 126 are actuated with two separate actuation rods 130a, 130b that reciprocate coaxially within the hollow sheath 37 in response to manipulation of two separate movable handles 34a, 34b by the user, shown in FIG. 18A and FIG. 19. Moving the handles 34a, 34b away from the stationary handle 35 pushes the actuator rods 130a, 130b backward in the direction of 80, shown in FIG. 18A and this backward motion of the actuator rods 130a, 130b causes the drive elements 116, 126 to rotate downward and upward, respectively, thereby opening the first and second movable jaw sets 110, 120. Since there are two separate handles 34a, 34b that can be moved separate from each other the motion of the two jaw sets is controlled independently from each other. The location of pivot pin 125 connecting drive elements 116, 126 to the housing 140 is varied by an additional pivot driver mechanism 160, as was described above. This additional pivot drive mechanism 160 allows the second jaw elements 114, 124 to move relative to the corresponding first jaw elements 112, 122 by activating the lever 60 in the direction 80. FIG. 16A-FIG. 16C depict several positions of the two movable jaw sets relative to each other and the corresponding jaw elements relative to each other. In this embodiment jaw sets 110, 120 move independently from each other and non-symmetrically to each other.

Figure 20:
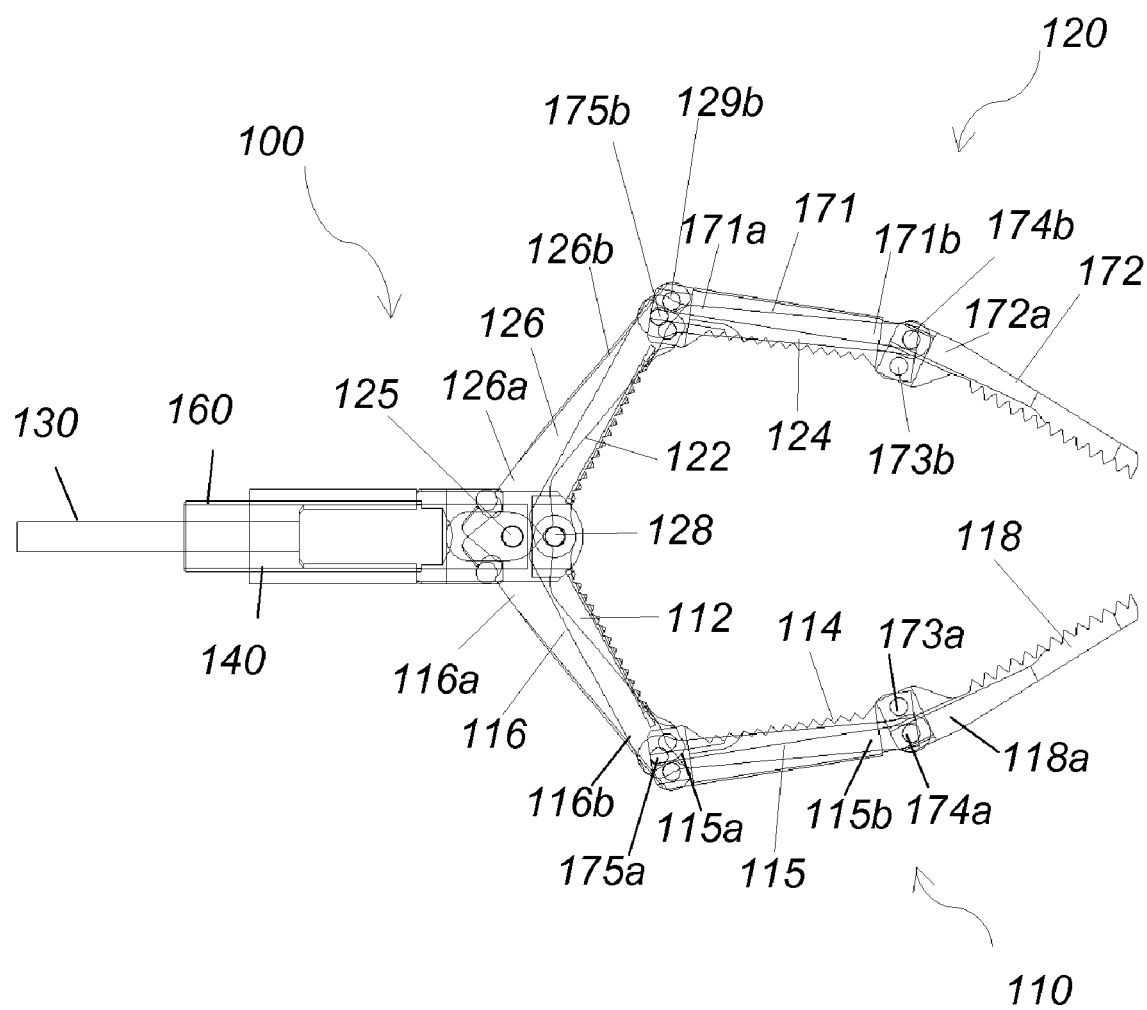
FIG. 20 is a transparent side view of a fifth embodiment of an improved end effector mechanism.
Figure 21A:
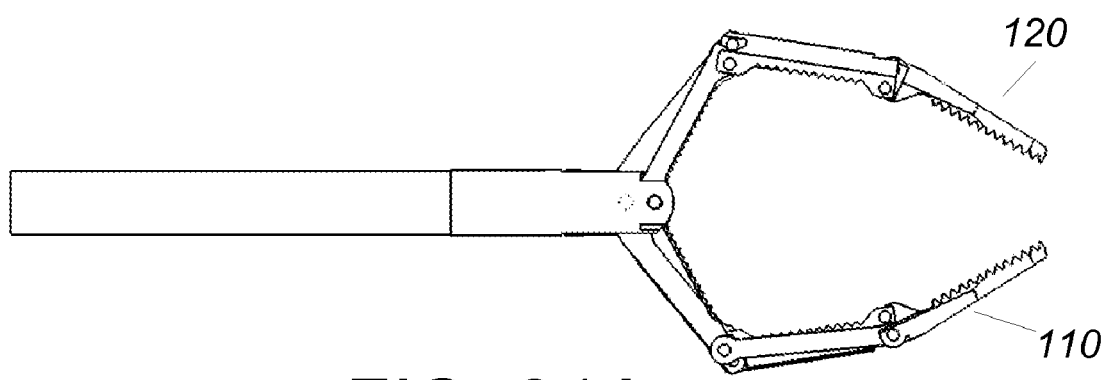
FIG. 21A is a side view of the end effector mechanism of FIG. 20 with the top jaw open forming a first angle with the lower jaw.
Figure 21B:
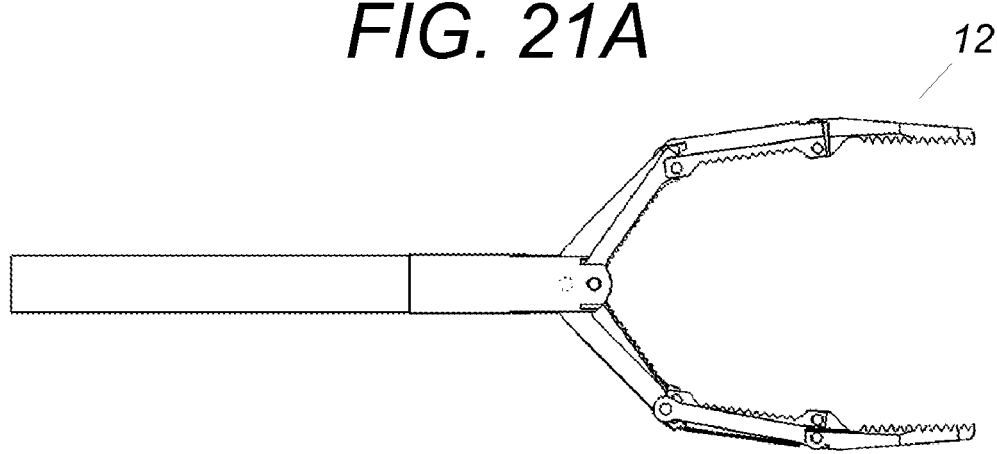
FIG. 21B is a side view of the end effector mechanism of FIG. 20 with the top jaw open forming a second angle with the lower jaw.
Figure 21C:
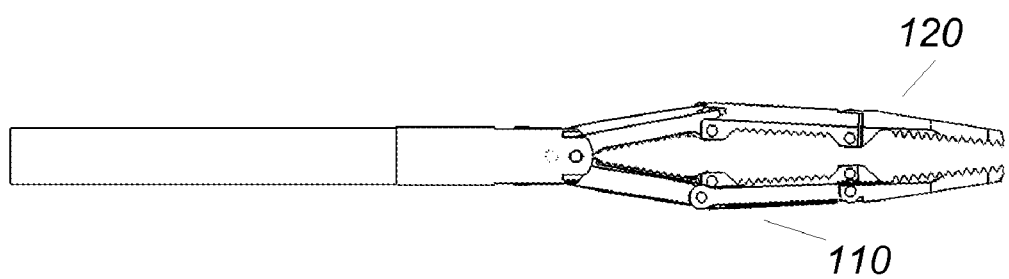
FIG. 21C is a side view of the end effector mechanism of FIG. 20 with the top jaw partially closed relative to the lower jaw.
Figure 21D:
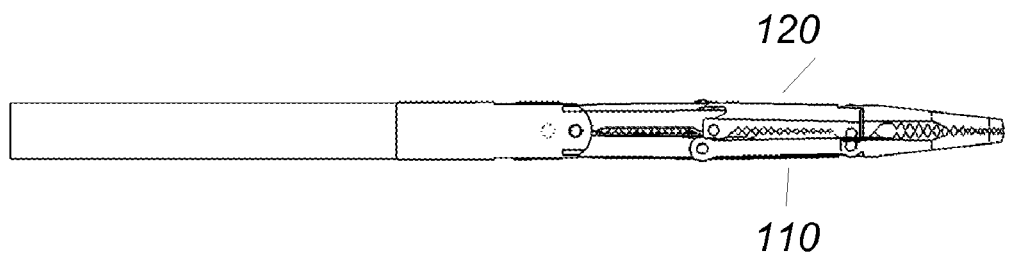
FIG. 21D is a side view of the end effector mechanism of FIG. 20 with the top jaw closed relative to the lower jaw.
Figure 22:
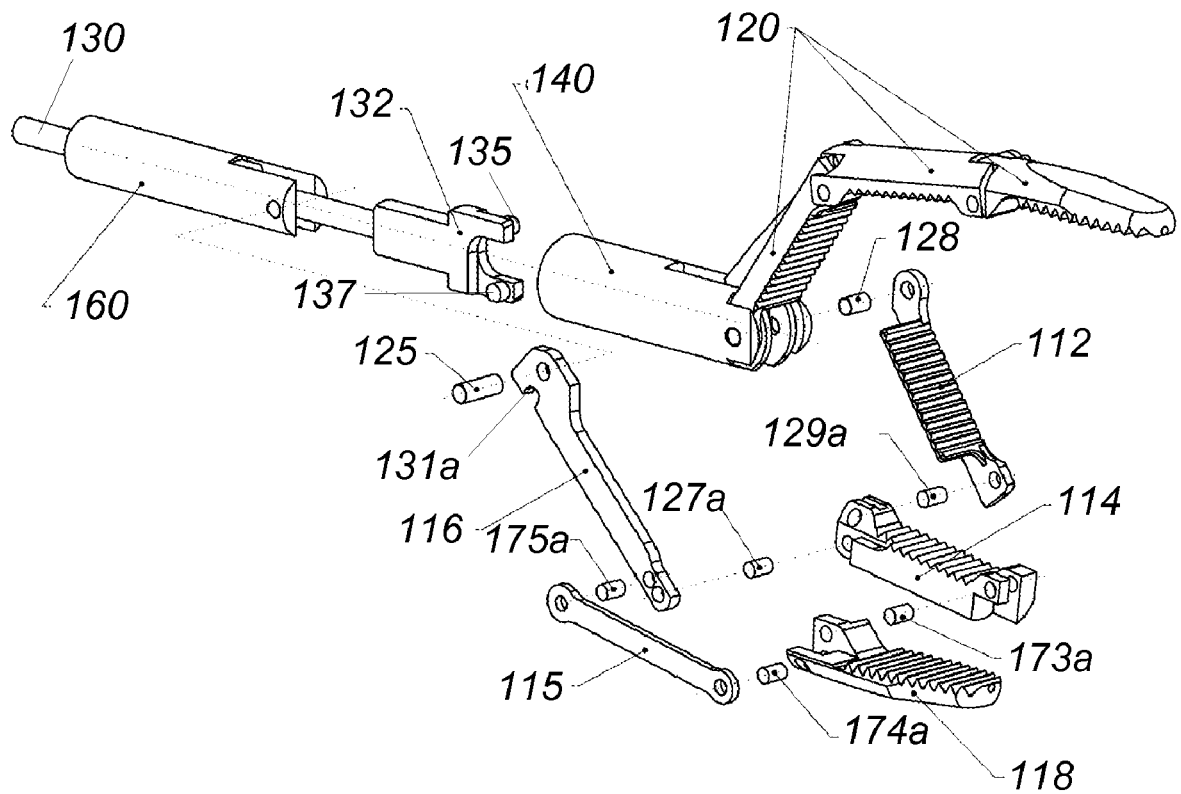
FIG. 22 is an exploded view of the end effector mechanism of FIG. 20.

Referring to FIG. 20 and FIG. 22 a fifth embodiment of the end effector mechanism 100, includes first and second sets of movable jaws 110, 120. First set of movable jaws 110 includes first, second and third jaw elements 112, 114, 118 drive element 116 and link element 115. Second set of movable jaws 120 includes first, second and third jaw elements 122, 124, 172, drive element 126 and link element 171. The second ends 116b, 126b of drive elements 116, 126 are pivotally connected to the first ends 115a, 171a of link elements 115, 171 with pivot pins 175a, 175b. The second ends 115b, 171b of link elements 115, 171 are pivotally connected to the third jaw elements 118, 172 with pivot pins 174a, 174b. First jaw elements 112, 122 are also pivotally connected to the second jaw elements 114, 124 with pivot pins 129a, 129b and second jaw elements 122, 124 are also pivotally connected to the third jaw elements 118, 172, with pivot pins 173a, 173b, respectively. First jaw elements 112, 124 are also pivotally connected to the housing 140 with pivot pin 128 and drive elements 116, 126 are also pivotally connected to the housing 140 with pivot pin 125. Both drive elements 116, 126 are also rotatively connected to actuator 132 by engaging yoke pins 135, 137 with the yoke links 131a, 131b, respectively, and are actuated with one actuation rod 130 that reciprocates coaxially within the hollow sheath 37 in response to manipulation of the movable handle 34 by the user. Moving the handle 34 away from the stationary handle 35 pushes the actuator rod 130 backward in the direction of 80, shown in FIG. 10C and this backward motion of the actuator rod 130 causes the drive elements 116, 126 to rotate downward and upward, respectively, thereby opening the first jaw elements 112, 122 of first and second movable jaw sets 110, 120, respectively. The motion of the first jaw elements 112, 122 is transferred to the second 114, 124 and third jaw elements 118, 172, via the link elements 115, 171, respectively. Since there is one actuator rod 130, the motion of the first jaw set 110 is mirror image to the motion of the second jaw set 120. The location of pivot pin 125 connecting drive elements 116, 126 to the housing 140 is varied by an additional pivot driver mechanism 160, as was described above. This additional pivot drive mechanism 160 allows the second jaw elements 114, 124 to move relative to the corresponding first jaw elements 112, 122 for each jaw set 110, 120. FIG. 21A-FIG. 21D depict several positions of the two movable jaw sets relative to each other and the corresponding jaw elements relative to each other.

Figure 23:
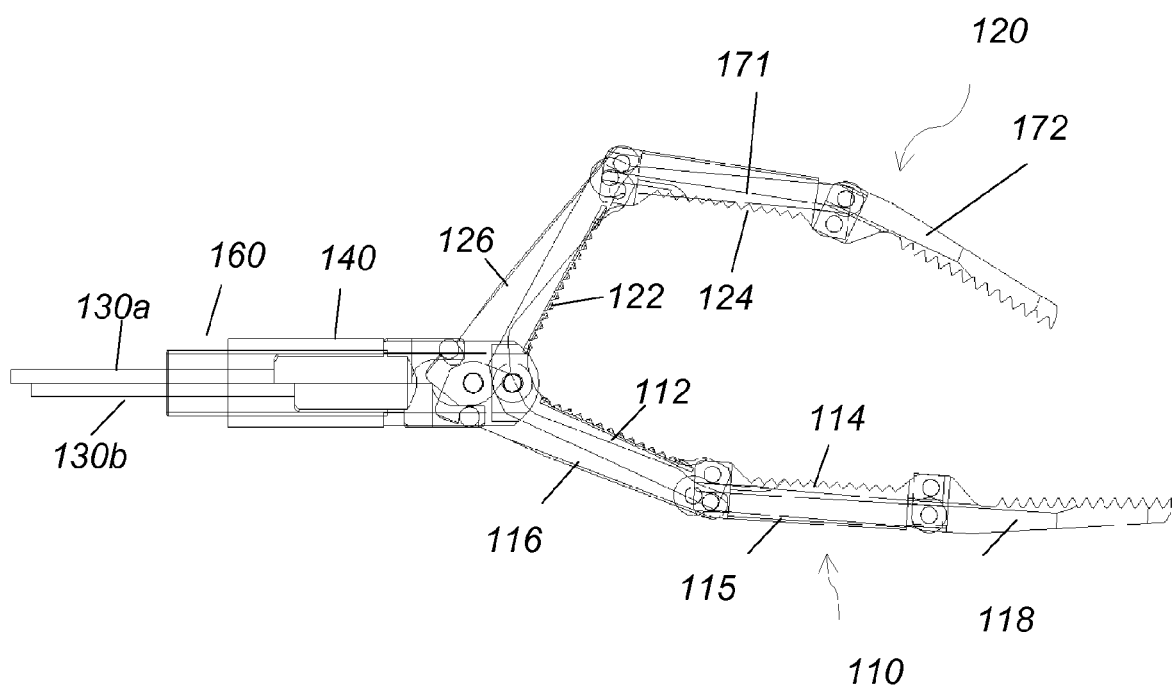
FIG. 23 is a transparent side view of a sixth embodiment of an improved end effector mechanism.
Figure 24A:
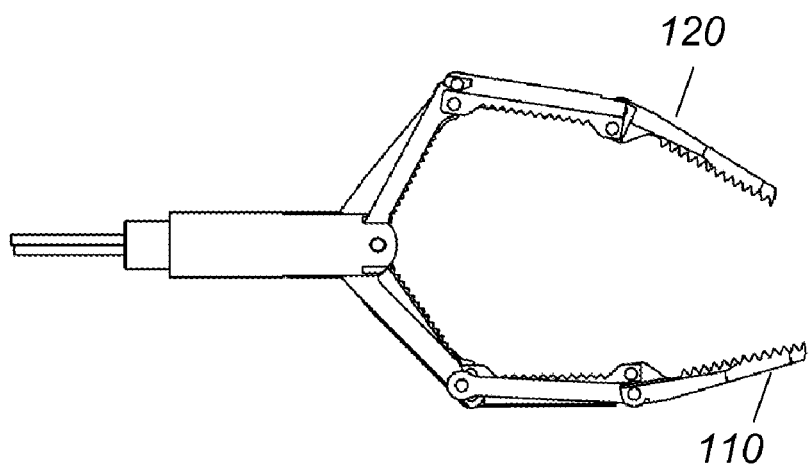
FIG. 24A is a side view of the end effector mechanism of FIG. 23 with the top jaw open forming a first angle with the lower jaw.
Figure 24B:
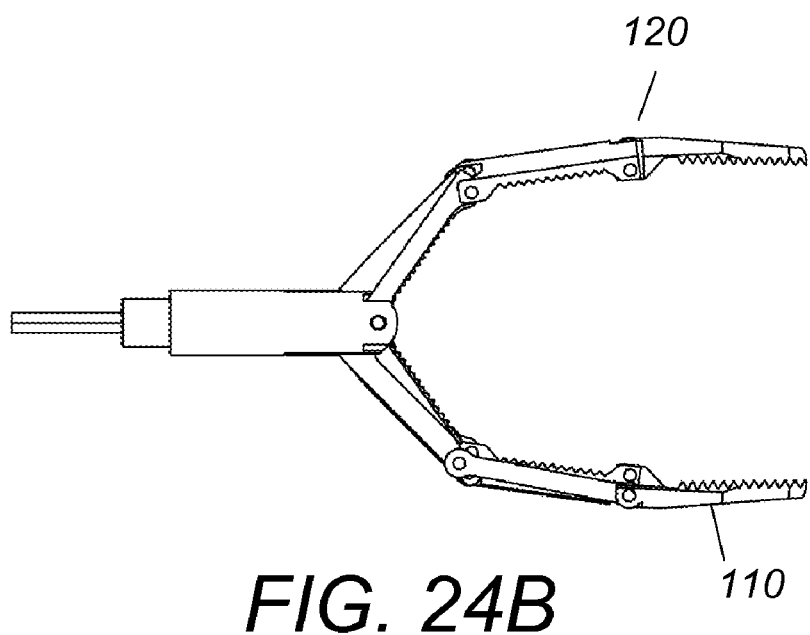
FIG. 24B is a side view of the end effector mechanism of FIG. 23 with the top jaw open forming a second angle with the lower jaw.
Figure 24C:
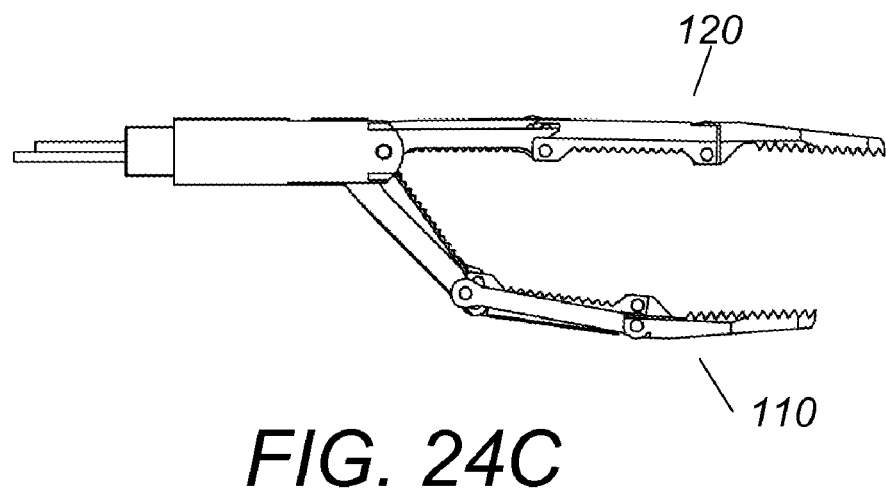
FIG. 24C is a side view of the end effector mechanism of FIG. 23 with the top jaw forming a third angle relative to the lower jaw.
Figure 25:
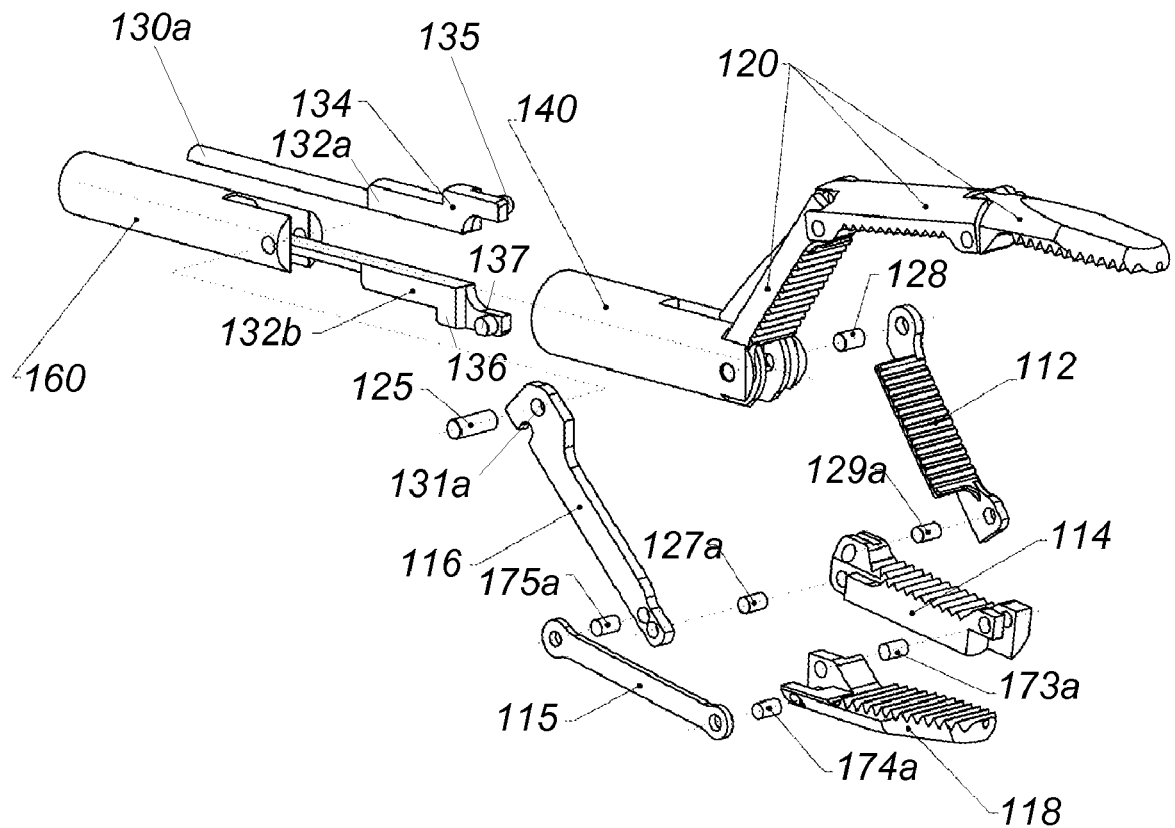
FIG. 25 is an exploded view of the end effector mechanism of FIG. 23.

Referring to FIG. 23 and FIG. 25 a sixth embodiment of the end effector mechanism 100, includes first and second sets of movable jaws 110, 120. First set of movable jaws 110 includes first, second and third jaw elements 112, 114, 118 drive element 116 and link element 115. Second set of movable jaws 120 includes first, second and third jaw elements 122, 124, 172, drive element 126 and link element 171. The second ends 116b, 126b of drive elements 116, 126 are pivotally connected to the first ends 115a, 171a of link elements 115, 171 with pivot pins 175a, 175b. The second ends 115b, 171b of link elements 115, 171 are pivotally connected to the third jaw elements 118, 172 with pivot pins 174a, 174b. First jaw elements 112, 122 are also pivotally connected to the second jaw elements 114, 124 with pivot pins 129a, 129b and second jaw elements 122, 124 are also pivotally connected to the third jaw elements 118, 172, with pivot pins 173a, 173b, respectively. First jaw elements 112, 124 are also pivotally connected to the housing 140 with pivot pin 128, as was described above. Drive elements 116, 126 are also pivotally connected to the housing 140 with pivot pin 125. Drive elements 126, 116 are also rotatively connected to actuators 132a, 132b by engaging yoke pins 135, 137 with the yoke links 131a, 131b, respectively, and are actuated with two separate actuation rods 130a, 130b that reciprocates coaxially within the hollow sheath 37 in response to manipulation of two separate movable handles 34a, 34b by the user, respectively. Moving the handles 34a, 34b away from the stationary handle 35 pushes the actuator rods 130a, 130b backward in the direction of 80, shown in FIG. 10C and this backward motion of the actuator rods 130a, 130b causes the drive elements 126, 116 to rotate upward or downward, thereby opening the first jaw elements 112, 122 of first and second movable jaw sets 110, 120, respectively. The motion of the first jaw elements 112, 122 is transferred to the second 114, 124 and third jaw elements 118, 172, via the link elements 115, 171, respectively. Since there are two actuator rods 130, 130b the motion of the first jaw set 110 is independent of the motion of the second jaw set 120 allowing for non-symmetric arrangement of the first jaw set relative to the second jaw set. The location of pivot pin 125 connecting drive elements 116, 126 to the housing 140 can be varied by an additional pivot driver mechanism 160, as was described above. This additional pivot drive mechanism 160 allows the second jaw elements 114, 124 to move relative to the corresponding first jaw elements 112, 122 for each jaw set 110, 120. FIG. 24A-FIG. 24C depict several positions of the two movable jaw sets relative to each other and the corresponding jaw elements relative to each other.

Figure 26:
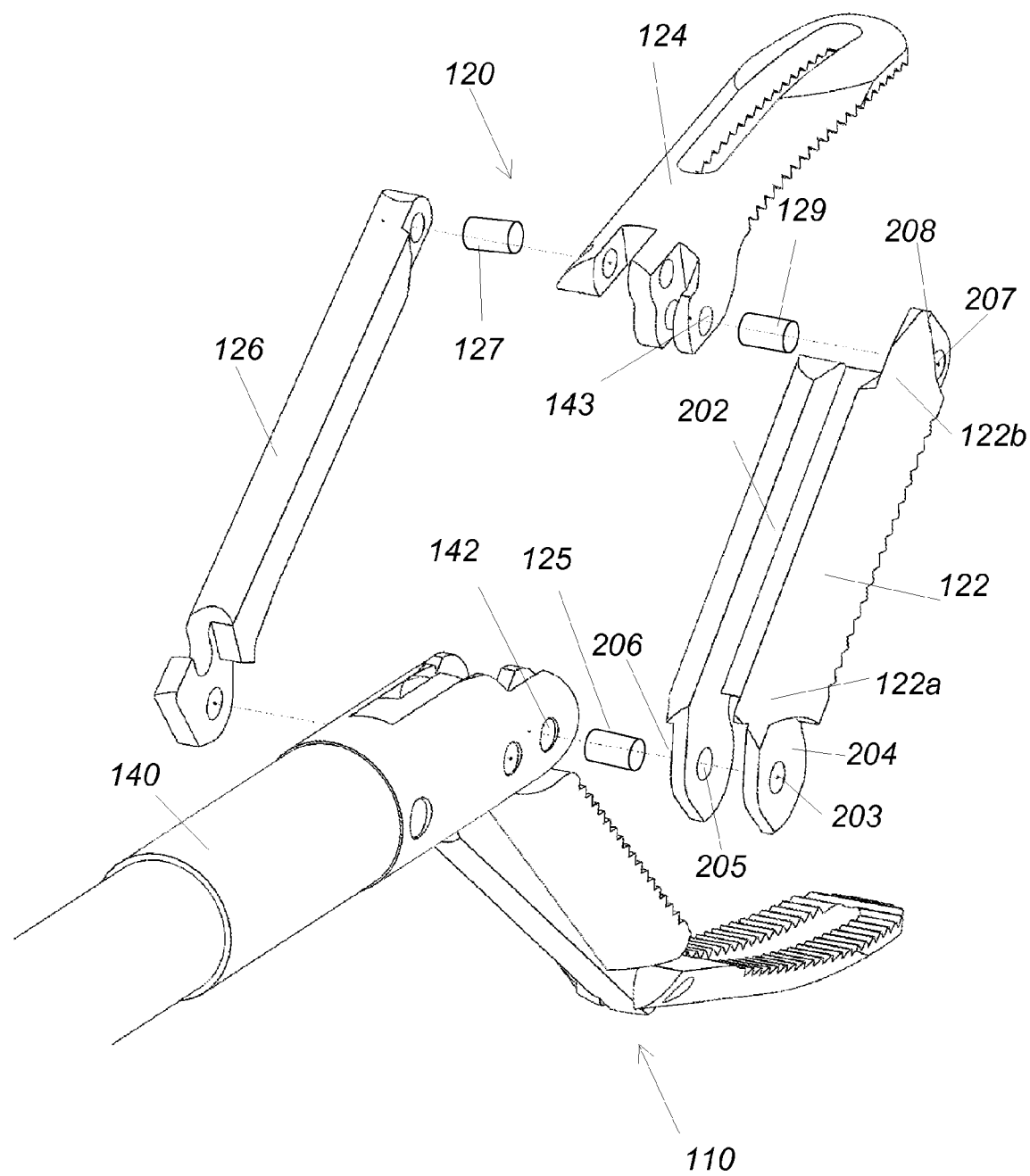
FIG. 26 is an exploded view of a seventh embodiment of an improved end effector mechanism.
Figure 27:
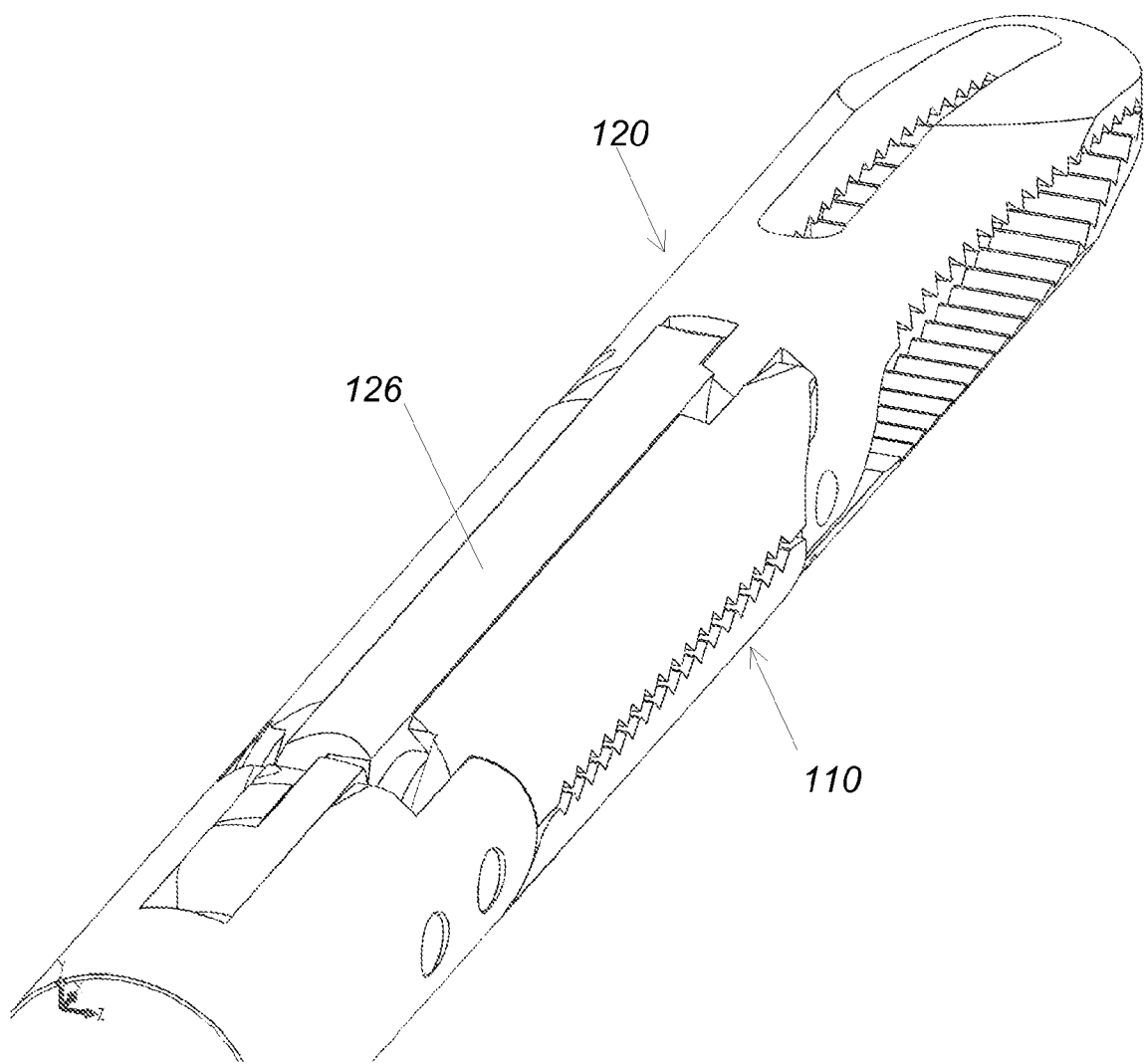
FIG. 27 depicts the end effector embodiment of FIG. 26 in the closed position.
Figure 28:
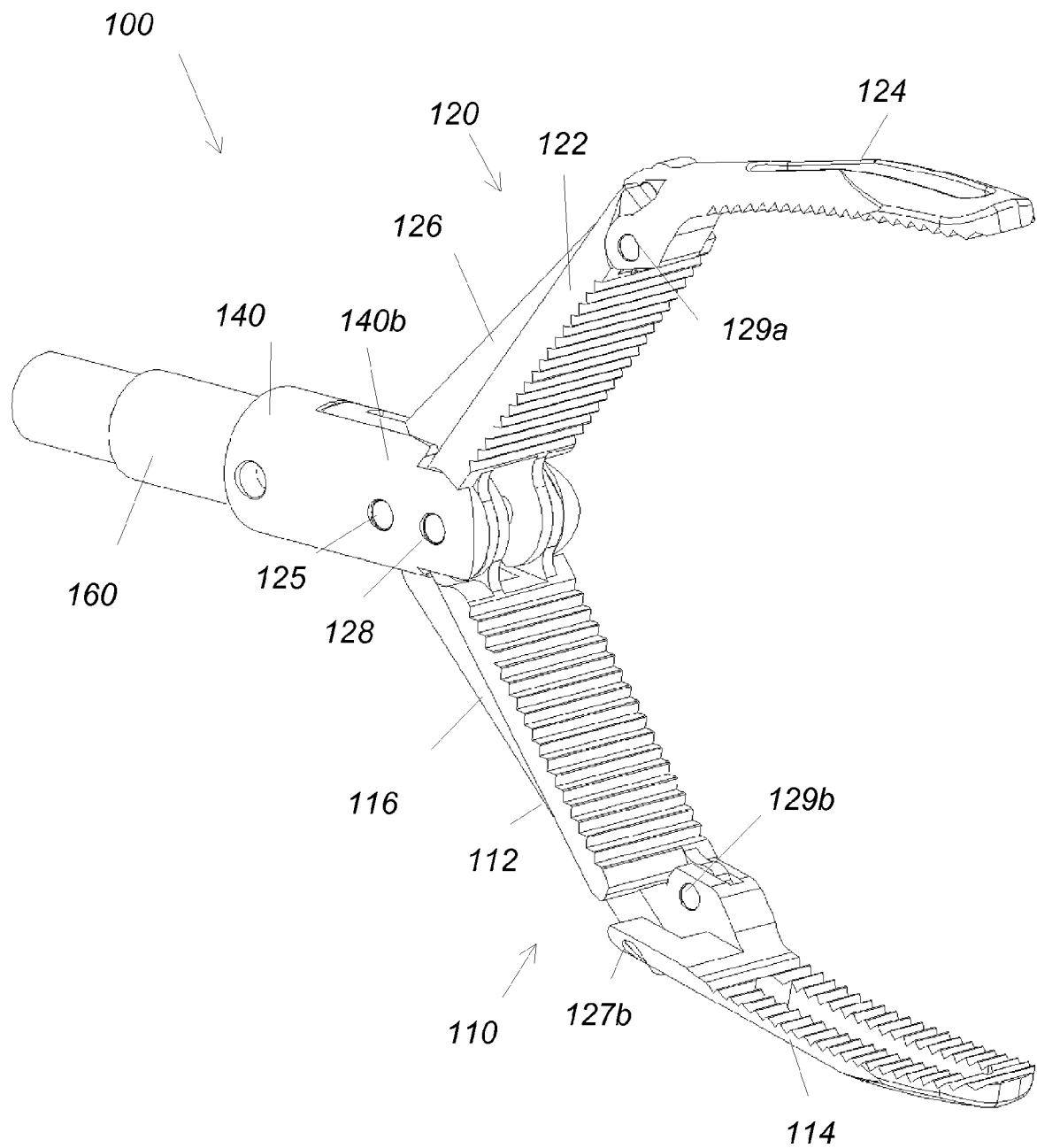
FIG. 28 is a perspective view of an eighth embodiment of an improved end effector mechanism.
Figure 29:
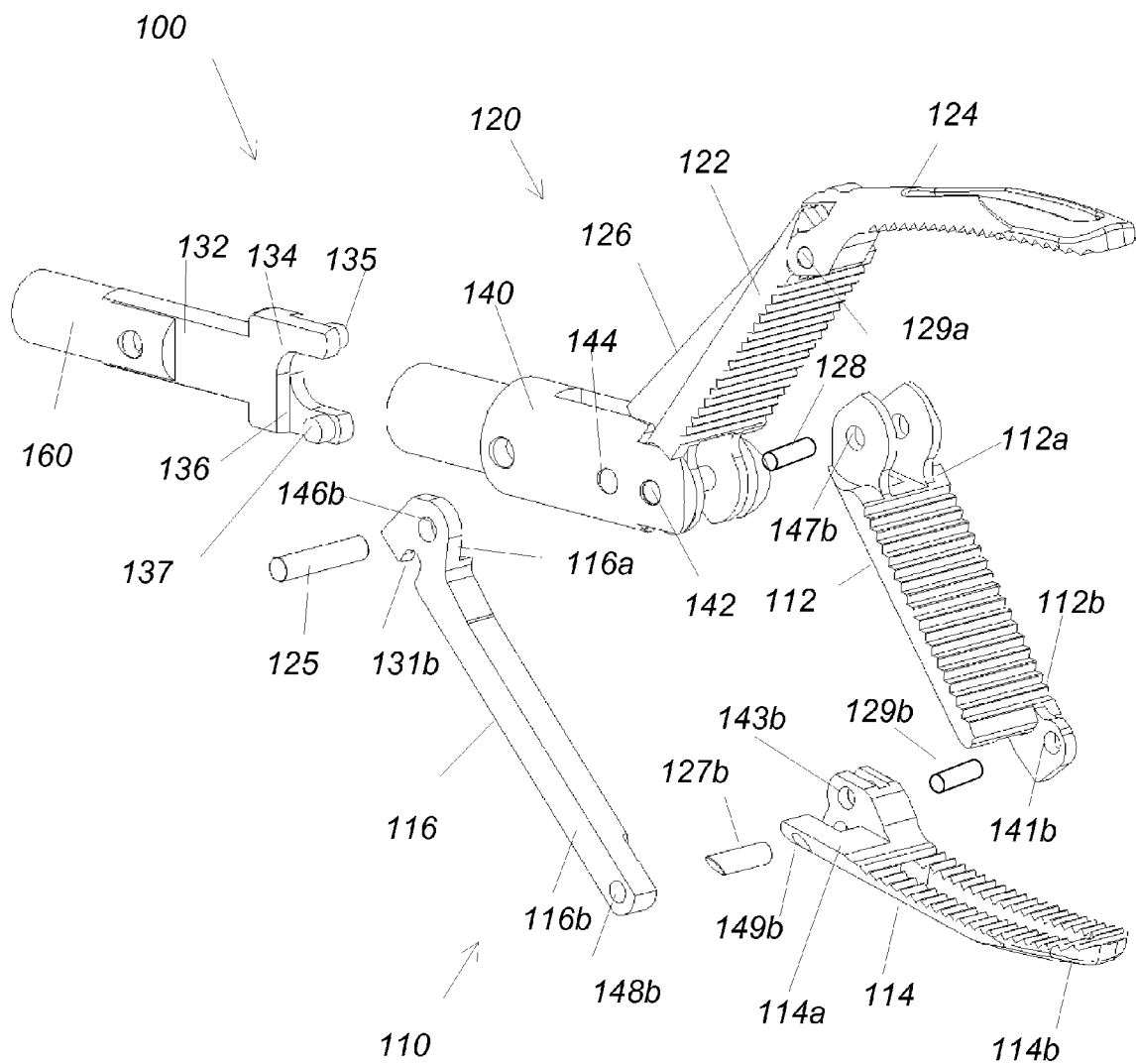
FIG. 29 is a partially exploded perspective view of the end effector mechanism of FIG. 28.
Figure 30:
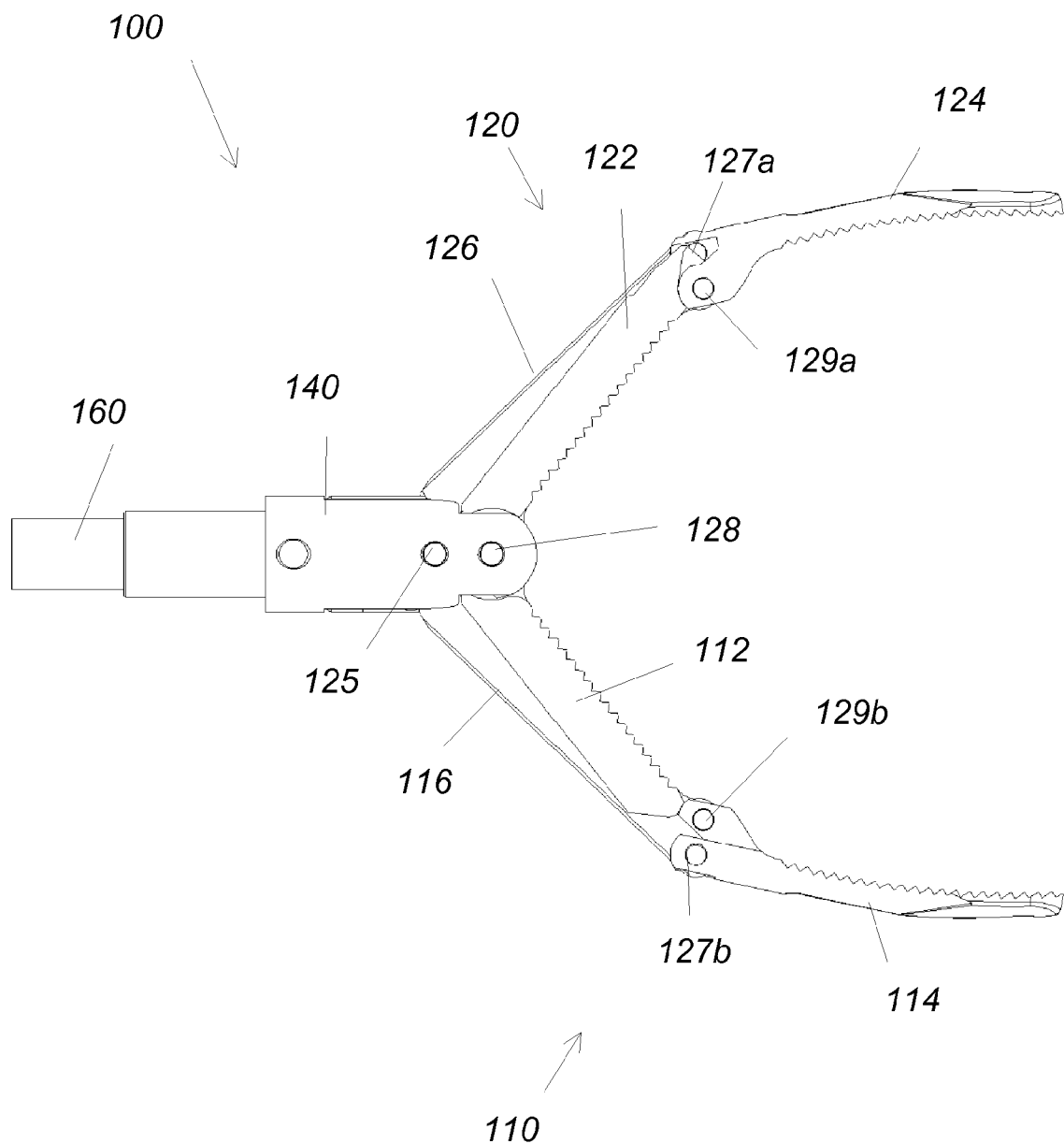
FIG. 30 is a side view of the end effector mechanism of FIG. 28.
Figure 31:
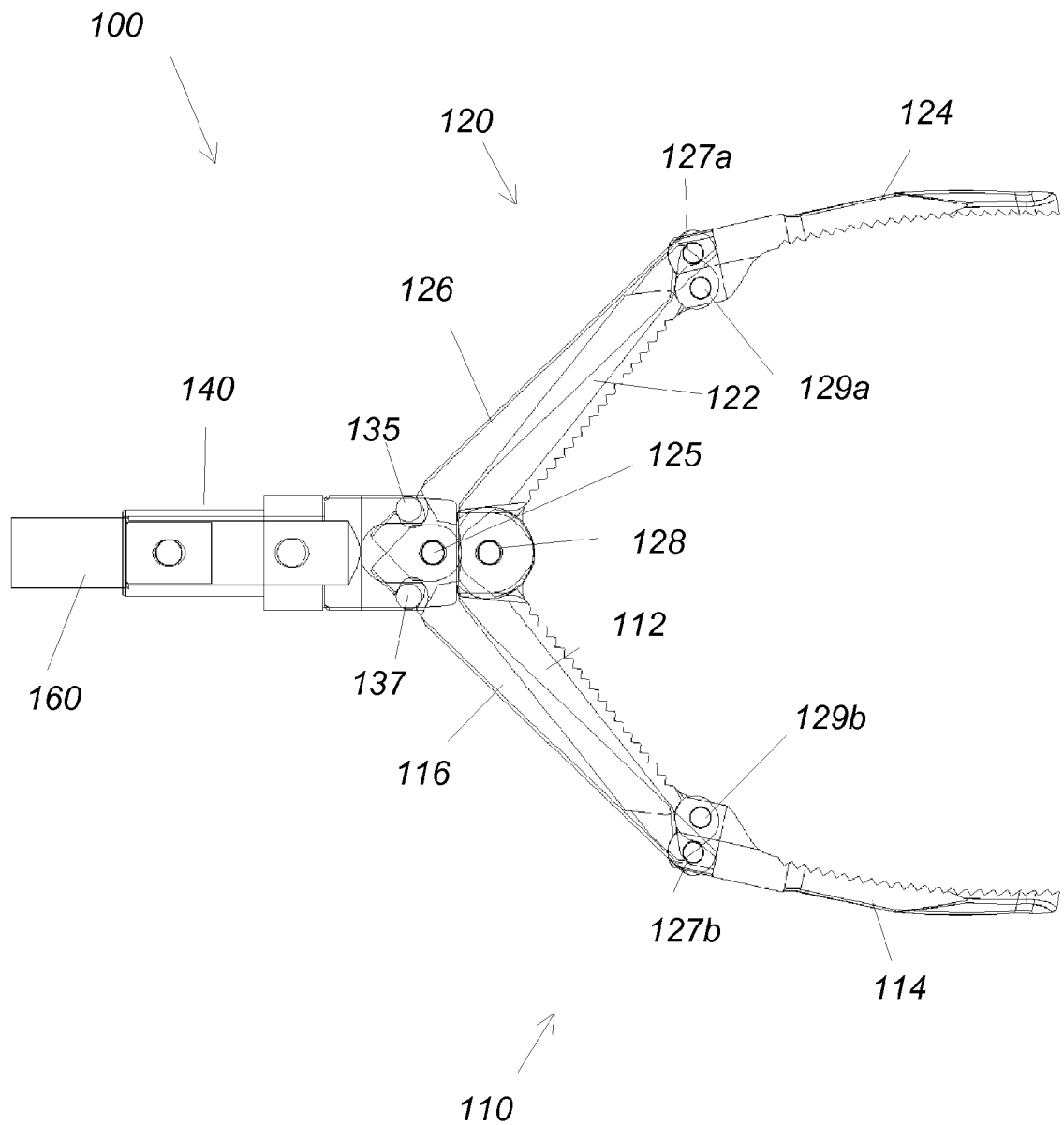
FIG. 31 is a transparent side view of the end effector mechanism of FIG. 28.

Referring to FIG. 26 and FIG. 27 in a seventh embodiment the first jaw element 122 of jaw set 120 includes an elongated groove 202 on a top surface. Groove 202 extends the entire length of the first jaw element and is dimensioned to accommodate the drive element 126, as shown in FIG. 26 and FIG. 27. Similarly, first jaw element 112 of jaw set 110 includes a groove (not shown) dimensioned to accommodate the drive element 116. The first end 122a of the first jaw element 122 has two flanges 204, 206 that connect pivotally to the housing end 140b by inserting a pivot pin 125 into through-opening 142 of the housing and into through openings 203 and 205 of the flanges 204 and 206, respectively. The second end 122b of the first jaw element 122 has one flange 208 that connects pivotally to the second jaw element 124 by inserting a pivot pin 129 into the through-opening 143 of the second jaw element and into through opening 207 of flange 208.

In one example, typical dimensions for the jaws are 0.500× 0.175 inches and typical dimensions for the handles are 0.230×4.5×1.75 inches. The endoscopic instrument may be made of various types of biocompatible stainless steels, ceramics, plastics, or composites. The end effector assembly may be disposable or non-disposable and may be made of various types of biocompatible stainless steels, metals, alloys, composites and plastics. As was mentioned above, the improved end effector mechanisms may be used in minimally invasive surgical instruments as well as instruments for general surgery or even as part of robotically controlled end effectors. It may also be used for applications in prosthetics, such as artificial finger joints and in other non-medical robotic applications.

In other embodiments, the end effector mechanism includes multiple sets of jaw elements paired with drive elements and link elements. Each jaw element also serves as a stabilizing link for the next most distal jaw element, forcing it to maintain its relative angle with respect to the opposing jaw elements. The jaw elements may have rounded surfaces, aggressive or atraumatic teeth, or incorporate an elbow and wide gripping surface. The dual action version of the end effector mechanism includes two or three jaw elements per side. The single action version includes two or three grasping elements opposing a fixed lower jaw. By adding means to adjust the distance between the main pivot pins in the housing and the pivot drive, the relative angle between the distal jaws is adjusted, either together, or independently. An independent control lever can be used to adjust the pivot center distance, or it can be tied to the main actuation mechanism through the use of a heavy override spring. Another method of adjusting the pivot center distance would be through the use of a tube within a tube arrangement, where a cam slot in the outer tube serves to move one of the pivot pins back and forth through rotary motion of the tube. Control over the jaw angles can serve to pinch the tips of the jaws together more or flatten them out depending on the application. A single main actuator can simultaneously control both opposing sets of jaw elements. Also, separate actuating rods can independently actuate each jaw element set. As was mentioned above both top and bottom sets of jaws are movable either symmetrical or non-symmetrical to each other.

Several embodiments of the present invention have been described. Nevertheless, it will be understood that various modifications may be made without departing from the spirit and scope of the invention. Accordingly, other embodiments are within the scope of the following claims.

What is claimed is:

1. A surgical instrument comprising an improved end effector assembly comprising:
   a housing;
   a pivot driver disposed within said housing and configured to reciprocate longitudinally within said housing;
   first and second gripping members extending from said housing;
   first actuation means for moving said first gripping member relative to said second gripping member, wherein said first actuation means comprise a first actuator being attached to a first end of a first actuator rod, and wherein said first actuator rod reciprocates longitudinally within said housing and within said pivot driver;
   wherein said first gripping member comprises a first jaw element, a second jaw element and a drive element and wherein said first jaw element comprises a first end pivotally connected to a first location of said housing and a second end pivotally connected to a first location of a first end of said second jaw element;
   wherein said drive element comprises a first end pivotally connected to a first location of said pivot driver and a second end pivotally connected to a second location of said first end of said second jaw element; and
   means for adjusting the distance between said first housing location and said first pivot driver location and wherein adjusting of said distance establishes a desired angular orientation between said first and second jaw elements.

2. The surgical instrument of claim 1 wherein said first gripping member drive element rotatively engages a first location of said first actuator and wherein linear motion of said first actuator rod translates into rotational motion of said first gripping member drive element and said rotational motion of said first gripping member drive element moves said first gripping member relative to said second gripping member.

3. The surgical instrument of claim 2 wherein said means for adjusting said distance between said first housing location and said first pivot driver location actuates longitudinal linear motion of said pivot driver and wherein said linear motion of said pivot driver translates into rotational motion of said first gripping member drive element and said rotational motion of said first gripping member drive element moves said first gripping member second jaw element relative to said first gripping member first jaw element.

4. The surgical instrument of claim 3 wherein said second gripping member comprises a first jaw element, a second jaw element and a drive element and wherein said second gripping member first jaw element comprises a first end pivotally connected to said first location of said housing and a second end pivotally connected to a first location of a first end of said second gripping member second jaw element and wherein said second gripping member drive element comprises a first end pivotally connected to said first location of said pivot driver and a second end pivotally connected to a second location of said first end of said second gripping member second jaw element.

5. The surgical instrument of claim 4 wherein said means for adjusting said distance between said first housing location and said first pivot driver location actuates longitudinal linear motion of said pivot driver and wherein said linear motion of said pivot driver translates into rotational motion of said second gripping member drive element and said rotational motion of said second gripping member drive element moves said second gripping member second jaw element relative to said second gripping member first jaw element.

6. The surgical instrument of claim 5 wherein said second gripping member drive element rotatively engages a second location of said first actuator and wherein linear motion of said first actuator rod translates into rotational motion of said second gripping member drive element and said rotational motion of said second gripping member drive element moves said second gripping member relative to said first gripping member.

7. The surgical instrument of claim 6 wherein said first actuator comprises first and second fingers, and wherein said first and second fingers comprise first and second yoke pins for rotatively engaging first and second linking yokes of the first and second gripping member drive elements, respectively.

8. The surgical instrument of claim 5 wherein said first actuation means further comprise a second actuator being attached to a first end of a second actuator rod, and wherein said second actuator rod reciprocates longitudinally within said housing and within said pivot driver and wherein said second gripping member drive element engages a first location of said second actuator and wherein linear motion of said second actuator rod translates into rotational motion of said second gripping member drive element and said rotational motion of said second gripping member drive element moves said second gripping member relative to said first gripping member.

9. The surgical instrument of claim 8 wherein said first and second actuators comprise first and second yoke pins for rotatively engaging first and second linking yokes of the first and second gripping member drive elements, respectively.

10. The surgical instrument of claim 3 further comprising a handle assembly for actuating said first actuation means and said means for adjusting said distance between said first housing location and said first pivot driver location.

11. The surgical instrument of claim 10 further comprising a shaft assembly comprising a hollow sheath, said first actuation means and said means for adjusting said distance between said first housing location and said first pivot driver location.

12. The surgical instrument of claim 1 wherein said pivot driver comprises a hollow tube.

13. The surgical instrument of claim 1 wherein said first gripping member further comprises a third jaw element and a second drive element and wherein said third jaw element comprises a first end pivotally connected to a first location of said second end of said second jaw element, and wherein said second drive element comprises a first end pivotally connected to a second location of said first end of said second jaw element and a second end pivotally connected to a second location of said first end of said third jaw element.

14. The surgical instrument of claim 13 further comprising additional jaw elements and additional drive elements for each of said first and second gripping members.

15. The surgical instrument of claim 1 wherein any of said jaw elements comprise inner surfaces comprising one of serrations, aggressive teeth, atraumatic teeth, elbow or protrusions.

16. The surgical instrument of claim 1 wherein any of said gripping members is disposable.

17. The surgical instrument of claim 1 wherein said second gripping member is fixedly connected to said housing.

18. The surgical instrument of claim 1 wherein said end effector assembly is robotically controlled.

19. The surgical instrument of claim 1 wherein said end effector assembly is used in minimally invasive surgery.

20. A prosthetic assembly comprising said improved end effector assembly of claim 1.

21. A robotic assembly comprising said improved end effector assembly of claim 1.

22. A method for setting any desired angular orientation between first and second jaw elements of a first gripping member of an end effector assembly for a surgical instrument, said method comprising:
  providing a housing;
  providing a pivot driver disposed within said housing and configured to reciprocate longitudinally within said housing;
  providing said first gripping member and a second gripping member wherein said first gripping member comprises said first and second jaw elements and a drive element;
  providing first actuation means for moving said first gripping member relative to said second gripping member, wherein said first actuation means comprise a first actuator being attached to a first end of a first actuator rod, and wherein said first actuator rod reciprocates longitudinally within said housing and within said pivot driver;
  pivotally connecting a first end of said first jaw element to a first location of said housing and a second end of said first jaw element to a first location of a first end of said second jaw element;
  pivotally connecting a first end of said drive element to a first location of said pivot driver and a second end of said drive element to a second location of said first end of said second jaw element, wherein said first housing location and said first pivot driver location are separated by an adjustable distance;
  providing means for adjusting said distance between said first housing location and said first pivot driver location; and
  adjusting the distance between said first housing location and said first pivot driver location thereby establishing a desired angular orientations between said first and second jaw elements.

* * * * *